United States Patent
Comer et al.

(10) Patent No.: US 11,911,444 B2
(45) Date of Patent: Feb. 27, 2024

(54) USE OF HUMAN SKIN SUBSTITUTES EXPRESSING EXOGENOUS IL-12 TO TREAT A WOUND BED

(71) Applicant: Stratatech Corporation, Madison, WI (US)

(72) Inventors: Allen R. Comer, Madison, WI (US); B. Lynn Allen-Hoffmann, Madison, WI (US)

(73) Assignee: Stratatech Corporation, Madison, WI (US)

(*) Notice: Subject to any disclaimer, the term of this patent is extended or adjusted under 35 U.S.C. 154(b) by 730 days.

(21) Appl. No.: 16/150,048

(22) Filed: Oct. 2, 2018

(65) Prior Publication Data
US 2019/0030130 A1  Jan. 31, 2019

Related U.S. Application Data

(63) Continuation of application No. 12/784,699, filed on May 21, 2010, now abandoned.

(60) Provisional application No. 61/180,250, filed on May 21, 2009.

(51) Int. Cl.
*A61K 48/00* (2006.01)
*A61K 38/20* (2006.01)
*C07K 14/54* (2006.01)
*C12N 5/071* (2010.01)
*A61K 35/12* (2015.01)

(52) U.S. Cl.
CPC ........ *A61K 38/208* (2013.01); *C07K 14/5434* (2013.01); *C12N 5/0629* (2013.01); *A61K 35/12* (2013.01); *A61K 48/00* (2013.01); *C12N 2501/23* (2013.01); *C12N 2510/00* (2013.01)

(58) Field of Classification Search
CPC .. A61K 38/208; A61K 48/00; C07K 14/5434; C12N 5/0629; C12N 2510/00
See application file for complete search history.

(56) References Cited

U.S. PATENT DOCUMENTS

| | | | |
|---|---|---|---|
| 4,485,096 A | 11/1984 | Bell | |
| 5,536,656 A | 7/1996 | Kemp | |
| 5,693,332 A | 12/1997 | Hansbrough | |
| 5,968,546 A | 10/1999 | Baur | |
| 5,989,837 A | 11/1999 | Allen-Hoffmann | |
| 6,039,760 A | 3/2000 | Eisenberg | |
| 6,214,567 B1 | 4/2001 | Allen-Hoffmann | |
| 6,485,724 B2 | 11/2002 | Allen-Hoffmann | |
| 6,495,135 B2 | 12/2002 | Allen-Hoffmann | |
| 6,514,711 B2 | 2/2003 | Allen-Hoffmann | |
| 6,846,675 B2 | 1/2005 | Conrad | |
| 6,974,697 B2 | 12/2005 | Comer | |
| 7,407,805 B2 | 8/2008 | Comer | |
| 7,462,448 B2 | 12/2008 | Allen-Hoffmann | |
| 7,498,167 B2 | 3/2009 | Comer | |
| 7,501,238 B2 | 3/2009 | Comer | |
| 7,541,188 B2 | 6/2009 | Conrad | |
| 7,674,291 B2 | 3/2010 | Centanni | |
| 7,807,148 B2 | 10/2010 | Comer | |
| 7,888,496 B2 | 2/2011 | Allen-Hoffmann | |
| 7,915,042 B2 | 3/2011 | Comer | |
| 7,955,790 B2 | 6/2011 | Comer | |
| 7,988,959 B2 | 8/2011 | Allen-Hoffmann | |
| 2006/0222635 A1 | 10/2006 | Centanni | |
| 2006/0257383 A1 | 11/2006 | Allen-Hofmann | |
| 2006/0258001 A1 | 11/2006 | Allen-Hoffmann | |
| 2009/0145087 A1 | 6/2009 | Allen-Hoffmann | |
| 2010/0119495 A1 | 5/2010 | Centanni | |
| 2010/0119615 A1 | 5/2010 | Comer | |
| 2010/0330046 A1 | 12/2010 | Comer | |

FOREIGN PATENT DOCUMENTS

| | | |
|---|---|---|
| WO | 02/070729 | 9/2002 |
| WO | 03/093418 | 11/2003 |
| WO | 04/110372 | 2/2004 |
| WO | 2004013606 A2 | 2/2004 |
| WO | 04/013606 | 12/2004 |
| WO | 2004110372 A2 | 12/2004 |
| WO | 05/012492 | 2/2005 |
| WO | 06/055931 | 5/2006 |
| WO | 06/094070 | 9/2006 |
| WO | 06/101834 | 9/2006 |
| WO | 09/065005 | 5/2009 |
| WO | 2010035948 A1 | 4/2010 |
| WO | 10/035948 | 5/2010 |
| WO | 10/135655 | 11/2010 |

OTHER PUBLICATIONS

Supp et al. Engineered skin substitutes: practices and potentials. Clin Dermatol. Jul.-Aug. 2005;23(4):403-12.*
Nagai et al. Antitumor effects on mouse melanoma elicited by local secretion of interleukin-12 and their enhancement by treatment with interleukin-18. Cancer Investigation, 2000, 18(3): 206-213.*
Lieschke et al. Bioactive murine and human interleukin-12 fusion proteins which retain antitumor activity in vivo. Nat Biotechnol. Jan. 1997;15(1):35-40.*
Thivolet et al. Cultured Human Epidermal Allografts are not Rejected for a Long Period. Arch Dermatol Res (1986) 278: 252-254.*
Gielen et al. Progressive Replacement of Human Cultured Epithelial Allografts by Recipient Cells as Evidenced by HLA Class I Antigens Expression. Dermatologica, 1987;175: 166-170.*

(Continued)

*Primary Examiner* — Dong Jiang

(57) ABSTRACT

The present invention relates generally to compositions for treating patients that have skin cancer or have recently had skin cancers removed. More specifically, the present invention provides human skin substitutes engineered to express exogenous IL-12 and compositions and methods for making human skin substitutes engineered to express exogenous IL-12. In addition, the present invention provides methods for treatment of sites on a patient where skin cancers have been removed with human skin substitutes engineered to express exogenous IL-12.

9 Claims, 12 Drawing Sheets

Specification includes a Sequence Listing.

(56) References Cited

OTHER PUBLICATIONS

Falanga et al. Rapid healing of venous ulcers and lack of clinical rejection with an allogeneic cultured human skin equivalent. Human Skin Equivalent Investigators Group. Arch Dermatol. 1998;134: 293-300.*

Ansell, S.M., et al., Randomized phase II study of interleukin-12 in combination with rituximab in previously treated non-Hodgkin's lymphoma patients. Clin Cancer Res, 2006. 12(20 Pt 1): p. 6056-63.

Aragane, Y., et al., IL-12 is expressed and released by human keratinocytes and epidermoid carcinoma cell lines. J Immunol, 1994. 153(12): p. 5366-72.

Baden, In Vitro Cell. Dev. Biol. 23(3):205-213 (1987).

Boukamp, et al., J. Cell. Boil. 106:761-771 (1988).

Colombo, M.P. and G. Trinchieri, Interleukin-12 in anti-tumor immunity and immunotherapy. Cytokine Growth Factor Rev, 2002. 13(2): p. 155-68.

Curran, M.P. and G.L. Plosker, Bilayered bioengineered skin substitute (Apligraf): a review of its use in the treatment of venous leg ulcers and diabetic foot ulcers. BioDrugs, 2002. 16(6): p. 439-55.

Eaglstein, W.H., M. Iriondo, and K. Laszlo, A composite skin substitute (graftskin) for surgical wounds. A clinical experience. Dermatol Surg, 1995. 21(10): p. 839-43.

Gillessen, S., et al., Mouse interleukin-12 (IL-12) p40 homodimer: a potent IL-12 antagonist. Eur J Immunol, 1995. 25 (1): p. 200-6.

Heinzerling, L., et al., Intratumoral injection of DNA encoding human interleukin 12 into patients with metastatic melanoma: clinical efficacy. Hum Gene Ther, 2005. 16(1): p. 35-48.

Lenzi, R., et al., Phase I study of intraperitoneal recombinant human interleukin 12 in patients with Mullerian carcinoma, gastrointestinal primary malignancies, and mesothelioma. Clin Cancer Res, 2002. 8(12): p. 3686-95.

Leonard, J.P., et al., Effects of single-dose interleukin-12 exposure on interleukin-12-associated toxicity and interferon-gamma production. Blood, 1997. 90(7): p. 2541-8.

Ling, P., et al., Human IL-12 p40 homodimer binds to the IL-12 receptor but does not mediate biologic activity. J Immunol, 1995. 154(1): p. 116-27.

Schoenhaut, D.S., et al., Cloning and expression of murine IL-12. J Immunol, 1992. 148(11): p. 3433- 40.

Schwarz, et al., "Interleukin-12 suppresses ultraviolet radiation-induced a poptosis by inducing DNA repair," Nat. Cell. Biol. (2002), vol. 4, No. 1, pp. 26-31.

Tahara, H., et al., "Fibroblasts genetically engineered to secrete interleukin 12 can suppress tumor growth and induce antitumor immunity to a murine melanoma in vivo," Cancer Res., (1994), vol. 54, pp. 182-189.

Trent, J.F. and R.S. Kirsner, Tissue engineered skin: Apligraf, a bi-layered living skin equivalent. International Journal of Clinical Practice, 1998. 52(6): p. 408-413.

Weiss, J.M., et al., Immunotherapy of cancer by IL-12-based cytokine combinations. Expert Opin Biol Ther, 2007. 7 (11): p. 1705-21.

Werth, V.P., et al., "IL-12 completely blocks ultraviolet-induced secretion of tumor necrosis factor a from cultured skin fibroblasts and keratinocytes," J. Invest. Dermatol. (2003), vol. 120, No. 1, pp. 116-122.

Wilkins, L.M., et al., Development of a Bilayered Living Skin Construct For Clinical Applications. Biotechnology and Bioengineering, 1994. 43(8): p. 747-756.

Zitvogel, L., et al., "Cancer Immunotherapy of Established Tumors with IL-12," J. Immunol., (1995), vol. 155, pp. 1393-1403.

Robertson, M.J. et al. Immunological effects of interleukin 12 administered by bolus intravenous injection to patients with cancer. Clinical cancer research : an official journal of the American Association for Cancer Research 5, 9-16 (1999).duction. Blood 90, 2541-2548 (1997).

Cohen, J. IL-12 deaths: explanation and a puzzle. Science (New York, N.Y.) 270, 908 (1995).

Car, B.D., Eng, V.M., Lipman, J.M. & Anderson, T.D. The toxicology of interleukin-12: a review. Toxicologic pathology 27, 58-63 (1999).

Mahvi, D.M. et al. Intratumoral injection of IL-12 plasmid DNA-results of a phase I/IB clinical trial. Cancer gene therapy 14, 717-723 (2007).

Lenzi, R. et al. Phase II study of intraperitoneal recombinant interleukin-12 (rhIL-12) in patients with peritoneal carcinomatosis (residual disease < 1 cm) associated with ovarian cancer or primary peritoneal carcinoma. Journal of translational medicine 5, 66 (2007).

Van Herpen, C.M. et al. Intratumoral recombinant human interleukin-12 administration in head and neck squamous cell carcinoma patients modifies locoregional lymph node architecture and induces natural killer cell infiltration in the primary tumor. Clinical cancer research : an official journal of the American Association for Cancer Research 11, 1899-1909 (2005).

Leonard, J.P. et al. Effects of single-dose interleukin-12 exposure on interleukin-12-associated toxicity and interferon-gamma production. Blood 90, 2541-2548 (1997).

Daud A.I., et al., "Phase I Trial of Interleukin-12 Plasmid Electroporation in Patients with Metastatic Melanoma," Journal of Clinical Oncology, Dec. 20, 2008, vol. 26 (36), pp. 5896-5903.

Gubler U., et al., "Coexpression of Two Distinct Genes is Required to Generate Secreted Bioactive Cytotoxic Lymphocyte Maturation Factor," Proceedings of the National Academy of Sciences of the United States of America, May 1991, vol. 88, pp. 4143-4147.

Heinzerling L., et al., "Intratumoral Injection of DNA Encoding Human Interleukin 12 Into Patients With Metastatic Melanoma: Clinical Efficacy," Human Gene Therapy, Jan. 2005, vol. 16, pp. 35-48.

Mahvi D.M., et al., "Intratumoral Injection of IL-12 Plasmid DNA—Results of A Phase I/I B Clinical Trial," Cancer Gene Herapy, 2007, vol. 14, pp. 717-723.

Van Herpen C.M.L., et al., "Intratumoral Recombinant Human Interleukin-12 Administration in Head and Neck Squamous Cell Carcinoma Patients Modifies Locoregional Lymph Node Architecture and Induces Natural Killer Cell Infiltration in the Primary Tumor," Clinical Cancer Research: An Official Journal of The American Association for Cancer Research, Mar. 1, 2005, vol. 11, pp. 1899-1909.

Schwarz A., et al., "Interleukin-12 Suppresses Ultraviolet Radiation-Induced Apoptosis By Inducing DNA Repair," Nature Cell Biology, 2001, vol. 4 (1), pp. 26-31.

* cited by examiner

Figure 1

SEQ ID NO:1

```
  1 mwppgsasqp ppspaaatgl hpaarpvslq crlsmcpars lllvatlvll dhlslarnlp
 61 vatpdpgmfp clhhsqnllr avsnmlqkar qtlefypcts eeidheditk dktstveacl
121 pleltknesc lnsretsfit ngsclasrkt sfmmalclss iyedlkmyqv efktmnakll
181 mdpkrqifld qnmlavidel mqalnfnset vpqkssleep dfyktkiklc illhafrira
241 vtidrvmsyl nas
```

SEQ ID NO:2

```
  1 mchqqlvisw fslvflaspl vaiwelkkdv yvveldwypd apgemvvltc dtpeedgitw
 61 tldqssevlg sgktltiqvk efgdagqytc hkggevlshs llllhkkedg iwstdilkdq
121 kepknktflr ceaknysgrf tcwwlttist dltfsvkssr gssdpqgvtc gaatlsaerv
181 rgdnkeyeys vecqedsacp aaeeslpiev mvdavhklky enytssffir diikpdppkn
241 lqlkplknsr qvevsweypd twstphsyfs ltfcvqvqgk skrekkdrvf tdktsatvic
301 rknasisvra qdryysssws ewasvpcs
```

Figure 2

SEQ ID NO:3 mchqqlvisw fslvflaspl vaiwelkkdv yvveldwypd apgemvvltc dtpeedgitw
tldqssevlg sgktltiqvk efgdagqytc hkggevlshs llllhkkedg iwstdilkdq
kepknktflr ceaknysgrf tcwwlttist dltfsvkssr gssdpqgvtc gaatlsaerv
rgdnkeyeys vecqedsacp aaeeslpiev mvdavhklky enytssffir diikpdppkn
lqlkplknsr qvevsweypd twstphsyfs ltfcvqvqgk skrekkdrvf tdktsatvic
rknasisvra qdryyssswsewasvpcs gggggggs aarpvslq crlsmcpars lllvatlvll dhlslarnlp
vatpdpgmfp clhhsqnllr avsnmlqkar qtlefypcts eeidheditk dktstveacl pleltknesc lnsretsfit
ngsclasrkt sfmmalclss iyedlkmyqv efktmnakll mdpkrqifld qnmlavidel mqalnfnset
vpqkssleep dfyktkiklc illhafrira vtidrvmsyl nas

Figure 3A

SEQ ID NO:4 (IL-12A cDNA)

```
   1 cgggagttaa tccgaaagcg ccgcaagccc cgcgggccgg ccgcaccgca cgtgtcaccg
  61 agaagctgat gtagagagag acacagaagg agacagaaag caagagacca gagtcccggg
 121 aaagtcctgc cgcgcctcgg gacaattata aaaatgtggc ccctggggtc agcctcccag
 181 ccaccgccct cacctgccgc ggccacaggt ctgcatccag cggctcgccc tgtgtccctg
 241 cagtgccggc tcagcatgtg tccagcgcgc agcctcctcc ttgtggctac cctggtcctc
 301 ctggaccacc tcagtttggc cagaaacctc cccgtggcca ctccagaccc aggaatgttc
 361 ccatgccttc accactccca aaacctgctg agggccgtca gcaacatgct ccagaaggcc
 421 agacaaactc tagaatttta cccttgcact tctgaagaga ttgatcatga agatatcaca
 481 aaagataaaa ccagcacagt ggaggcctgt ttaccattgg aattaaccaa gaatgagagt
 541 tgcctaaatt ccagagagac ctctttcata actaatggga gttgcctggc ctccagaaag
 601 acctctttta tgatggccct gtgccttagt agtatttatg aagacttgaa gatgtaccag
 661 gtggagttca agaccatgaa tgcaaagctt ctgatggatc ctaagaggca gatctttcta
 721 gatcaaaaca tgctggcagt tattgatgag ctgatgcagg ccctgaattt caacagtgag
 781 actgtgccac aaaaatcctc ccttgaagaa ccggattttt ataaaactaa aatcaagctc
 841 tgcatacttc ttcatgcttt cagaattcgg gcagtgacta ttgatagagt gatgagctat
 901 ctgaatgctt cctaaaaagc gaggtccctc caaaccgttg tcatttttat aaaactttga
 961 aatgaggaaa ctttgatagg atgtggatta agaactaggg aggggaaag aaggatggga
1021 c
```

Figure 3B

SEQ ID NO:5 (IL-12B cDNA)

```
   1 ccattggact ctccgtcctg cccagagcaa gatgtgtcac cagcagttgg tcatctcttg
  61 gttttccctg gtttttctgg catctcccct cgtggccata tgggaactga agaaagatgt
 121 ttatgtcgta gaattggatt ggtatcccgga tgcccctgga gaatggtgg tcctcacctg
 181 tgacacccct gaagaagatg gtatcacctg gaccttggac cagagcagtg aggtcttagg
 241 ctctggcaaa accctgacca tccaagtcaa agagtttgga gatgctggcc agtacacctg
 301 tcacaaagga ggcgaggttc taagccattc gctcctgctg cttcacaaaa aggaagatgg
 361 aatttggtcc actgatattt taaaggacca gaaagaaccc aaaaataaga cctttctaag
 421 atgcgaggcc aagaattatt ctggacgttt cacctgctgg tggctgacga caatcagtac
 481 tgatttgaca ttcagtgtca aaagcagcag aggctcttct gaccccccaag gggtgacgtg
 541 cggagctgct acactctctg cagagagagt cagaggggac aacaaggagt atgagtactc
 601 agtggagtgc caggaggaca gtgcctgccc agctgctgag gagagtctgc ccattgaggt
 661 catggtggat gccgttcaca agctcaagta tgaaaactac accagcagct tcttcatcag
 721 ggacatcatc aaacctgacc cacccaagaa cttgcagctg aagccattaa agaattctcg
 781 gcaggtggag gtcagctggg agtaccctga cacctggagt actccacatt cctacttctc
 841 cctgacattc tgcgttcagg tccagggcaa gagcaagaga gaaaagaaag atagagtctt
 901 cacggacaag acctcagcca cggtcatctg ccgcaaaaat gccagcatta gcgtgcgggc
 961 ccaggaccgc tactatagct catcttggag cgaatgggca tctgtgccct gcagttaggt
1021 tctgatccag gatgaaaatt tggagg
```

Figure 4

SEQ ID NO 6: IL-12 fusion cgcgcggccgcgccaccatgtgtcaccagcagttggtcatctcttggttttccctggttttttctggcatct
cccctcgtggccatatgggaactgaagaaagatgtttatgtcgtagaattggattggtatccggatgcccc
tggagaaatggtggtcctcacctgtgacacccctgaagaagatggtatcacctggaccttggaccagagca
gtgaggtcttaggctctggcaaaaccctgaccatccaagtcaaagagtttggagatgctggccagtacacc
tgtcacaaaggaggcgaggttctaagccattcgctcctgctgcttcacaaaaaggaagatggaatttggtc
cactgatattttaaaggaccagaaagaacccaaaaataagacctttctaagatgcgaggccaagaattatt
ctggacgtttcacctgctggtggctgacgacaatcagtactgatttgacattcagtgtcaaaagcagcaga
ggctcttctgaccccaaggggtgacgtgcggagctgctacactctctgcagagagagtcagaggggacaa
caaggagtatgagtactcagtggagtgccaggaggacagtgcctgcccagctgctgaggagagtctgccca
ttgaggtcatggtggatgccgttcacaagctcaagtatgaaaactacaccagcagcttcttcatcaggac
atcatcaaacctgacccacccaagaacttgcagctgaagccattaaagaattctcggcaggtggaggtcag
ctgggagtaccctgacacctggagtactccacattcctacttctccctgacattctgcgttcaggtccagg
gcaagagcaagagagaaaagaaagatagagtcttcacggacaagacctcagccacggtcatctgccgcaaa
aatgccagcattagcgtgcgggcccaggaccgctactatagctcatcttggagcgaatgggcatctgtgcc
ctgcagtggaggtggcggtggaggctccgcggctcgccctgtgtccctgcagtgccggctcagcatgtgtc
cagcgcgcagcctcctccttgtggctaccctggtcctcctggaccacctcagtttggccagaaacctcccc
gtggccactccagacccaggaatgttcccatgccttcaccactcccaaaacctgctgagggccgtcagcaa
catgctccagaaggccagacaaactctagaatttttaccccttgcacttctgaagagattgatcatgaagata
tcacaaaagataaaaccagcacagtggaggcctgtttaccattggaattaaccaagaatgagagttgccta
aattccagagagacctctttcataactaatgggagttgcctggcctccagaaagacctcttttatgatggc
cctgtgccttagtagtatttatgaagacttgaagatgtaccaggtggagttcaagaccatgaatgcaaagc
ttctgatggatcctaagaggcagatctttctagatcaaaacatgctggcagttattgatgagctgatgcag
gccctgaatttcaacagtgagactgtgccacaaaaatcctcccttgaagaaccggatttttataaaactaa
aatcaagctctgcatacttcttcatgctttcagaattcgggcagtgactattgatagagtgatgagctatc
tgaatgcttcctaagcggccgccgc

Figure 10

| Analysis of transgene expression in stable NIKS[IL-12] clones | | | | | | | | | | | | | | |
|---|---|---|---|---|---|---|---|---|---|---|---|---|---|---|
| Construct | | INV | | | INV/Kozak | | | | | K14/Kozak | | | | |
| Clone # | | 1 | 3 | 4 | 5 | 6 | 7 | 8 | 9 | 11 | 12 | 13 | 14 | 15 |
| RT-PCR | | | | | | | | | | | | | | |
| ELISA (pg/mL) | pas s 3 | 1996 | 1 | 0 | 0 | 0 | 0 | 405 | 23 | 5942 | 3999 | 3620 | 62 | 148 |
| | pas s 6 | 3223 | 0 | 0 | 0 | 0 | 0 | 405 | 0 | 5034 | 2796 | 1999 | 0 | 114 |

USE OF HUMAN SKIN SUBSTITUTES EXPRESSING EXOGENOUS IL-12 TO TREAT A WOUND BED

CROSS REFERENCE TO RELATED APPLICATIONS

This application claims priority to U.S. Ser. No. 12/784,699, filed May 21, 2010, which claim the benefit of U.S. Provisional Application No. 61/180,250, filed May 21, 2009, the disclosures of which are incorporated herein by reference.

STATEMENT REGARDING FEDERALLY SPONSORED RESEARCH OR DEVELOPMENT

This invention was made with government support under SBIR Grant R44 CA139747 awarded by the National Institutes of Health. The government has certain rights in the invention.

FIELD OF THE INVENTION

The present invention relates generally to compositions for treating patients that have skin cancer or have recently had skin cancers removed. More specifically, the present invention provides human skin substitutes engineered to express exogenous IL-12 and compositions and methods for making human skin substitutes engineered to express exogenous IL-12. In addition, the present invention provides methods for treatment of sites on a patient where skin cancers have been removed with human skin substitutes engineered to express exogenous IL-12.

REFERENCE TO SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821(f).

BACKGROUND

Over half of all human cancers originate in stratified squamous epithelia. In epidermal and oral carcinogenesis, neoplastic cells originate near the basement membrane and progressively occupy the full thickness of the stratified squamous epithelium. The National Cancer Institute projects that more than 1,000,000 cases of skin cancer are expected to be diagnosed in the United States in 2008, including more than 62,000 new cases of melanoma. Deaths from melanoma are projected to number more than 8,400. While cutaneous SCC and BCC are rarely invasive, the American Cancer Society and American Society of Clinical Oncology estimate that 2,000-3,000 Americans die from non-melanoma skin cancer annually. Although surgical excision of the primary tumor is curative for the majority of squamous and basal cell skin cancers, approximately 10% of primary or recurrent non-melanoma skin cancers present as complex, perineural, or locally invasive tumors that are more difficult to manage by surgery alone. The use of Mohs' micrographic surgery to eliminate the tumor and adjacent areas of microscopically abnormal tissue has led to decreases in the rate of local tumor recurrence. However, tumor recurrence near the site of the primary tumor remains a predominant cause of treatment failure in these patients. Accordingly, there is an urgent need for novel strategies to eradicate residual tumor cells after resection of the primary tumor.

Decades of research into immunological responses to tumors have established the critical role that innate and adaptive immune responses play in suppressing the establishment and growth of human cancers [8]. According to the immune surveillance hypothesis [9, 10], a major function of the human immune system is to identify and eradicate cancerous cells before they become established tumors. Insight into mechanisms that regulate the recognition of tumor cells by the immune system coupled with the phenomenon of spontaneous, immune-mediated tumor regression [11] have led many investigators to explore various approaches to enhance the innate and adaptive immune responses to tumor cells and antigens. One approach that has received considerable attention is stimulation of anti-tumor responses with immunomodulatory cytokines, alone or in combination with other agents [12, 13]. One of the most promising cytokines for tumor immunotherapy is IL-12, due to its potent anti-tumor activity [12, 14], ability to synergize with other cytokines [13, 15], and role in stimulating both innate and adaptive tumor responses [16]. Although an argument against the potential efficacy of immunotherapy is that many established tumors have undergone selection to evade recognition by the immune system [8], cytokines such as IL-12 appear able to reverse the immunosuppressive environment of tumors and activate anti-tumor lymphocytes that reside in a quiescent state inside tumor tissue [14, 17-19].

SUMMARY OF THE INVENTION

The present invention relates generally to compositions for treating patients that have skin cancer or have recently had skin cancers removed. More specifically, the present invention provides human skin substitutes engineered to express exogenous IL-12 and compositions and methods for making human skin substitutes engineered to express exogenous IL-12. In addition, the present invention provides methods for treatment of sites on a patient where skin cancers have been removed with human skin substitutes engineered to express exogenous IL-12.

The present invention additionally provides a composition comprising host cells expressing heterologous IL-12, wherein the host cells are primary keratinocytes, keratinocyte precursors, immortalized keratinocytes, or transdifferentiated keratinocytes. In some preferred embodiments, host cells are selected from the group consisting of NIKS® cells and cells derived from NIKS® cells. In some embodiments, the compositions further comprise second host cells, wherein said second host cells express a second heterologous polypeptide.

In some embodiments, the Interleukin-12 is selected from the group consisting of proteins having subunits comprising SEQ ID NO:1 and SEQ ID NO:2 and proteins having subunits sharing at least 80%, 90%, 95, 97%, or 99% identity with SEQ ID NO:1 and SEQ ID NO:2. In some preferred embodiments, the IL-12 is fusion protein encompassing both IL-12 subunits, for example SEQ ID NO:3 and sequences having at least 80%, 90%, 95, 97%, or 99% identity with SEQ ID NO:3. In some embodiments, the cells are stably transfected with a gene expressing said IL-12.

In some embodiments, the gene encoding said heterologous Interleukin-12 is operably linked to a promoter sequence that allows Interleukin-12 expression in said skin substitute. In some embodiments, the promoter sequence is selected from the group consisting of a K14 promoter, an involucrin promoter, and an ubiquitin promoter.

In some embodiments, the composition is a cultured human skin substitute. In some embodiments, the composition produces amounts of bioactive IL-12 which are capable of inducing the proliferation of the PHA-stimulated lymphoblasts.

In some embodiments, the present invention provides methods of providing a human skin substitute expressing heterologous Interleukin-12, comprising: a) providing keratinocytes selected from the group consisting of primary keratinocytes, keratinocyte precursors, transdifferentiated keratinocytes, and immortalized keratinocytes and an expression vector comprising a DNA sequence encoding Interleukin-12 operably linked to a regulatory sequence; b) introducing said expression vector into said keratinocytes; and c) organotypically culturing said keratinocytes to provide a human skin substitute. In some embodiments, the keratinocytes are Near-Diploid Immortalized Keratinocytes and said keratinocytes stratify into squamous epithelia. In some embodiments, the methods further comprise comprising co-culturing said Near-Diploid Immortalized Keratinocytes cells with cells derived from a patient.

In some embodiments, the present invention provides methods of treating a patient comprising a) providing a human skin substitute comprising cells expressing heterologous Interleukin-12, wherein cells are selected from the group consisting of primary keratinocytes, keratinocyte precursors, transdifferentiated keratinocytes, and immortalized keratinocytes; and b) contacting said patient with said human skin substitute. In some embodiments, the patient has skin cancer. In some embodiments, the skin cancer is selected from the group consisting of melanoma and basal cell carcinoma. In some embodiments, the human skin substitute is applied to a site on said patient where a skin cancer has been removed. In some embodiments, the human skin substitute prevents or inhibits the spread of said skin cancer. In some embodiments, the human skin substitute produces amounts of bioactive IL-12 which are capable of inducing the proliferation of the PHA-stimulated lymphoblasts.

DESCRIPTION OF THE FIGURES

FIG. 1 provides the protein sequence for human IL-12A (p35) and B (p40) subunits (SEQ ID NOs:1 and 2).

FIG. 2 provides the sequence of an IL-12 fusion protein (SEQ ID NO:3).

FIG. 3A and FIG. 3B provide nucleic acid sequences. Specifically, FIG. 3A provides the nucleic acid sequence for human IL-12A (p35) (SEQ ID NO: 4) and FIG. 3B provides the nucleic acid sequence for human IL-12A (p40) subunit (SEQ ID NO: 5).

FIG. 4 provides the nucleic acid sequence (SEQ ID NO:6) encoding the IL-12 fusion protein (SEQ ID NO:3).

FIG. 6A: IL-12 mRNA expression in NIKS cultures transiently transfected for 24 hours with IL-12 constructs detailed in FIG. 10. RT-PCR amplification of mRNA from NIKS control (N) does not show detectable IL-12 transgene expression. FIG. 6B: Culture media conditioned for 24 or 72 hours with NIKS cells transiently transfected with the IL-12 expression constructs were assayed for IL-12 by ELISA.

FIG. 8A: IL-12 in tissue sections stained by immunohistochemistry. Sections were stained using anti-human-IL-12 Ab (purple). Sections were counterstained with methyl green nuclear counterstain (green). FIG. 8B: Quantification of IL-12 in conditioned media samples from organotypic tissues generated with NIKS cells or NIKS$^{IL-12}$ clones as determined by ELISA. FIG. 8C: Western blot analysis showing IL-12 expression in clones 1, 8, 9, 11, 12, 13, and 15. NIKS® (N) cells do not endogenously express detectable IL-12.

FIG. 10 shows the IL-12 mRNA expression and IL-12 protein expression of 15 clones over several passages.

DEFINITIONS

Figure 5:
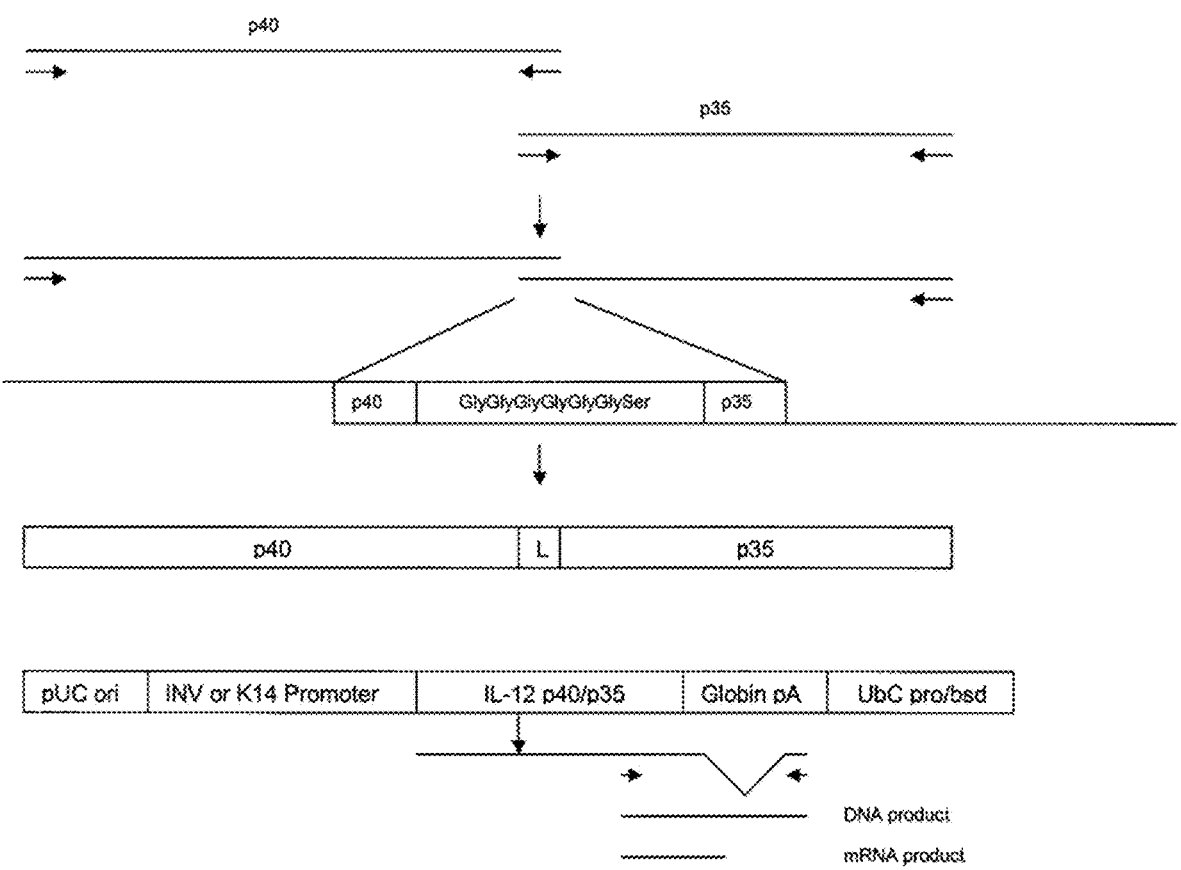
FIG. 5 provides a schematic diagram of a construct for expression of exogenous human IL-12 in a skin equivalent.

As used herein, the terms "interleukin-12" or "IL-12", when used in reference to a protein or nucleic acid refers to a protein or nucleic acid encoding a protein that shares greater than about 50% identity with either or both of SEQ ID NOs: 1 and 2 and also has at least one activity of wild type IL-12. Wild-type IL-12 comprises two subunits, A and B, which are also known as the p35 and p40 subunits, respectively. The term IL-12 as used herein encompasses protein comprising one or both of the two subunits. The term IL-12 as used herein also encompasses fusion proteins in which both subunits of IL-12 are expressed as a single fusion protein (e.g., SEQ ID NO: 3). Thus, the term IL-12 protein encompasses both proteins that are identical to wild-type IL-12 protein and those that are derived from wild type IL-12 protein (e.g., variants of IL-12 protein or chimeric genes constructed with portions of IL-12 protein coding regions).

As used herein, the term "activity of IL-12" refers to any activity of wild type IL-12 protein (e.g., stimulation of the activity of cytotoxic T lymphocytes (CTL) and natural killer (NK) cells or induction of expression of interferon-γ from these cells). The term is intended to encompass all activities of IL-12 protein, alone or in combination.

The terms "IL-12 gene" and "IL-12 nucleic acid sequence" refer to the IL-12 nucleotide sequence of either or both of the A and B subunits of IL-12 (e.g., SEQ ID NOs:4 and 5). Thus, the term IL-12 nucleic acid sequence or gene refers to a nucleic acid sequence for the A subunit of IL-12, the B subunit of IL-12, or both subunits. The terms IL-12 nucleic acid sequence and IL-12 gene also can refer to a nucleic acid sequence encoding a fusion of the A and B subunits (e.g., SEQ ID NO: 6), or a nucleic acid sequence in which the A and B subunits are separated by an IRES sequence. As used herein, these terms also encompass fragments of the IL-12 sequence, as well as other domains within the full-length IL-12 nucleotide sequence, as well as variants of IL-12. Furthermore, the terms "IL-12 gene nucleotide sequence" or "IL-12 gene polynucleotide sequence" encompasses DNA, cDNA, and RNA (e.g., mRNA) sequences.

As used herein, the term "NIKS® cells" refers to cells having the characteristics of the cells deposited as cell line ATCC CRL-12191.

As used herein, the term "keratinocyte precursor" refers to any cell type that can differentiate into a keratinocyte (e.g., pluripotent or totipotent cell type).

As used herein, the term "transdifferentiated keratinocyte" refers to any cell or cell type that results from the transdifferentiation of a primary keratinocyte or an immortalized keratinocyte.

The term "gene" refers to a nucleic acid (e.g., DNA) sequence that comprises coding sequences necessary for the production of a polypeptide or precursor (e.g., IL-12). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "recombinant DNA molecule" as used herein refers to a DNA molecule that is comprised of segments of DNA joined together by means of molecular biological techniques.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding IL-12 includes, by way of example, such nucleic acid in cells ordinarily expressing IL-12 where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein the term "coding region" when used in reference to a structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets that specify stop codons (i.e., TAA, TAG, TGA).

As used herein, the term "purified" or "to purify" refers to the removal of contaminants from a sample.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

A "regulatory sequence" refers to a polynucleotide sequence that is necessary for regulation of expression of a coding sequence to which the polynucleotide sequence is operably linked. The nature of such regulatory sequences differs depending upon the host organism. In prokaryotes, such regulatory sequences generally include, for example, a promoter, and/or a transcription termination sequence. In eukaryotes, generally, such regulatory sequences include, for example, a promoter and/or a transcription termination sequence. The term "regulatory sequence" may also include additional components, the presence of which are advantageous, for example, a secretory leader sequence for secretion of the polypeptide attached thereto.

"Operably linked" refers to a juxtaposition wherein the components so described are in a relationship permitting them to function in their intended manner. A regulatory sequence is "operably linked" to a coding sequence when it is joined in such a way that expression of the coding sequence is achieved under conditions compatible with the regulatory sequence.

As used herein, the term "host cell" refers to any eukaryotic or prokaryotic cell (e.g., bacterial cells such as E. coli, yeast cells, mammalian cells, avian cells, amphibian cells, plant cells, fish cells, and insect cells), whether located in vitro or in vivo. For example, host cells may be located in a transgenic animal.

The terms "overexpression" and "overexpressing" and grammatical equivalents, are used in reference to levels of mRNA to indicate a level of expression higher (e.g., at least 2 fold and preferably at least 3 fold higher) than that typically observed in a given tissue in a control or non-transgenic animal. Levels of mRNA are measured using any of a number of techniques known to those skilled in the art including, but not limited to Northern blot or reverse transcription analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the IL-12 mRNA-specific signal observed on Northern blots). The amount of mRNA present in the band corresponding in size to the correctly spliced IL-12 transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA does not integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]) has been modified by several groups to optimize conditions for particular types of cells. The art is well aware of these numerous modifications.

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

DETAILED DESCRIPTION

The present invention provides a composition comprising host cells expressing exogenous IL-12, wherein the host cells are primary keratinocytes, keratinocyte precursors, immortalized keratinocytes, or transdifferentiated keratinocytes (e.g., NIKS® cells or cells derived from NIKS® cells). In some preferred embodiments, the IL-12 is fusion protein containing both IL-12 subunits. In some embodiments, the cells are stably transfected with a gene expressing said IL-12.

Human IL-12 is a potent immunomodulatory cytokine that stimulates the activity of CTL and NK cells, induces expression of interferon-γ from these cells, and promotes the initiation and maintenance of Th1 responses [12, 13, 20]. IL-12 is produced by activated dendritic cells, macrophages, and B cells as a heterodimeric cytokine composed of disulfide-linked p35 and p40 subunits. The p40 subunit also dimerizes with IL-23 p19 to form the IL-23 cytokine [16, 21]. The p40 subunit can also form homodimers that are expressed in excess relative to the IL-12 and IL-23 heterodimers and that can inhibit the activity of both IL-12 and IL-23 [16, 22-24]. Several groups have shown that the p40 and p35 subunits can be expressed as a single-chain fusion protein and that the chimeric p40/p35 IL-12 protein has bioactivity comparable to the disulfide linked heterodimer [25-27] thereby eliminating the production of inhibitory p40 homodimers.

The high-affinity IL-12 receptor is a heterodimer composed of IL-12Rβ1 and IL-12Rβ2 subunits, both of which are members of the gp130 subgroup of cytokine receptors [12, 28]. Expression of the IL-12 receptors is subject to positive feedback such that receptor expression is up-regulated following stimulation by IL-12 [29, 30]. IL-12 signaling occurs via activation of both STAT4 and STAT3 and results in the induction of IFN-γ, which is responsible for driving the development of a Th1 response and downstream IL-12 dependent immunostimulatory effects [12]. The ability of phagocytes and dendritic cells to produce IL-12 is potentiated by IFN-γ, providing another mechanism by which the IL-12 signaling pathway is amplified in response to an initial stimulus [31]. The induction of IFN-γ by IL-12 also results in anti-angiogenic effects mediated by downstream effectors such as IFN-γ-inducible protein 10 and monokine-induced by IFN-γ [12, 32].

Numerous studies have demonstrated that IL-12 stimulates both innate and adaptive immune responses to tumor cells (reviewed in [12, 16, 33]). In mice, local or systemic administration of murine IL-12 promotes infiltration of tumors by lymphocytes, enhances the cytotoxic activity of CTLs and NK cells, and leads to increased levels of IFN-γ.

IL-12 displays synergistic tumor suppressive activity with a number of other cytokines (reviewed in [13]). In particular, combined administration of IL-12 and IL-2 shows a synergistic enhancement of T cell responses and inhibition of tumor growth [34]. Recently, several groups have demonstrated that local production of IL-12 by genetically modified cells can suppress the growth of experimental tumors [35-37]. Eliopoulos et al. demonstrated that mesenchymal stromal cells (MSC) modified to produce IL-12 suppressed the growth of murine 4T1 breast cancer cells and B 16 melanoma cells when implanted adjacent to the tumor, but not when implanted at distant sites [37]. Similarly, Chen et al. found that IL-12 expressing MSCs migrated to established tumors and inhibited their growth and metastasis without systemic toxicity that was seen using systemic IL-12 administration [35]. Using skin flaps genetically modified to express IL-12, Dempsey et al. demonstrated that local production of IL-12 from the flaps was able to suppress the growth of subcutaneously injected tumor cells [36]. Tumor suppression was associated with increases in local, but not systemic, levels of IL-12 and IFN-γ. These and other studies using biodegradable IL-12 microspheres [14, 17, 18, 38] suggest therapeutic approaches whereby sustained local production of IL-12 may circumvent the toxicity seen with repeated bolus systemic administration of IL-12.

The anti-tumor activity of IL-12 is indirect, in that it requires activation of CTLs, NK cells and increased production of IFN-γ from activated lymphocytes. Although murine IL-12 stimulates proliferation and IFN-γ production in PHA-activated human lymphoblasts, human IL-12 does not exhibit biological activity in mice [39]. Therefore, several chimeric animal models have been developed to study the anti-tumor activity of human IL-12 in mice containing xenografts of human tumor cells and human lymphocytes. Mixed xenografts of human peripheral blood lymphocytes (HuPBL) and human tumors in SCID mice have been used to study the activation of anti-tumor responses in human lymphocytes by IL-12 [15, 38]. Using this system, it has been shown that local or systemic administration of IL-12 suppresses tumor growth by enhancing the cytotoxicity of co-engrafted human CTL [15, 38].

It has recently been shown that local administration of IL-12 is able to activate tumor-associated effector/memory T cells that exist in a quiescent state in the immunosuppressed microenvironment of established murine and human tumors [14, 17-19]. Kilinc et al. found that, in addition to promoting activation of latent effector/memory T cells, IL-12 promotes apoptosis of T suppressor cells and leads to infiltration of the tumors by CD8+ effector T cells [19]. Using samples of non-disrupted human lung tumors transplanted into SCID mice, Broderick et al. demonstrated that IL-12 stimulates quiescent effector memory T cells residing in the tumor tissue to proliferate and invade tumor-rich tissue, resulting in rapid eradication of the tumor [17]. Thus, IL-12 appears able to reverse the immunosuppressive microenvironment of human tumors and promotes the expansion and activity of tumor-reactive lymphocytes that exist in a quiescent state in many tumors. The ability of IL-12 to re-activate this latent immune response, as well as promote new anti-tumor activity in naïve lymphocytes, demonstrates the potential therapeutic benefits of IL-12 immunotherapy.

Based on its potent ability to inhibit tumor growth in animal models, the safety and efficacy of IL-12 has been evaluated in human clinical trials using both recombinant IL-12 and gene therapy approaches. In a Phase I study using intravenous administration of rhIL-12 into patients with advanced malignancy, it was found that an initial dose of IL-12 (500 ng/kg) followed two weeks later by 5 consecutive daily doses at the same level was tolerated with acceptable safety. However, during a subsequent Phase 2 trial, repeated daily administration of IL-12 at the same dose led to serious adverse events in 12 patients, two of whom died due to severe toxicity associated with systemic elevations of IFN-γ [1]. Subsequent studies determined that administration of the initial IL-12 dose followed by a 2 week rest period, which was not included in the Phase 2 trial, attenuated the IFN-γ response to subsequent IL-12 doses. Therefore, the toxicity of systemically-administered IL-12 is highly dependent on dosing schedule. Based on an understanding of the schedule-dependent toxicity seen in initial IL-12 trials, subsequent clinical trials of IL-12 have been performed with reduced IL-12 doses or a reduced frequency of administration [2, 3]. While toxicity associated with the modified treatment regimens were less than the initial studies, the efficacy of systemically-administered rhIL-12 has generally been modest [2, 3]. The limited efficacy seen in these studies may be related to the relatively short half life of IL-12 administered as purified protein [4]. Early stage clinical studies using intra-tumoral injection of IL-12 plasmid DNA suggests this approach may demonstrate efficacy [5, 6], but these preliminary studies await confirmation in larger, controlled studies.

The present invention provides a novel approach for treating patients with skin cancer, and patients from which skin cancers have been recently removed, with a graft that delivers IL-12 to the site of the skin cancer or recently removed skin cancer. In some embodiments, the skin substitute is a durable, suturable combination tissue product that is manufactured with a particular shape and size, (e.g., circular patches with a surface area of 44 cm2). In some embodiments, the skin substitute is a multi-layered skin substitute with hallmarks of a normal differentiating epidermis. In some embodiments, a single layer of cuboidal basal cells rests at the junction of the epidermis and the dermal equivalent. The rounded morphology and high nuclear to cytoplasmic ratio of these cells is indicative of an actively dividing population of keratinocytes. Suprabasal to the proliferating keratinocytes is a layer of flattened spinous cells. Above the spinous layer is a well-defined granular layer with cells containing dark keratohyalin granules. The uppermost layers of the skin substitute consist of densely packed enucleated corneocytes that form the stratum corneum.

In some embodiments, the skin substitute is an allograft. In some embodiments, the skin substitute is not incorporated onto the patient as a permanent graft. However, in some embodiments, the skin substitute persists in the wound bed long enough to promote sustained secretion of IL-12. Clinical experience to date with allogeneic bioengineered skin substitutes has shown that the cellular and biological components of cultured skin substitute tissue are poorly antigenic and do not undergo rejection or elicit immune responses in recipients [40-44]. Instead of being rejected, allogeneic keratinocytes are gradually absorbed into the wound bed and replaced by patient keratinocytes migrating in from the wound margin [45, 46]. The present invention is not limited to any particular mechanism of action. Indeed, an understanding of the mechanism of action is not required to practice the present invention. Nevertheless, it is likely that local expression of IL-12 by the genetically-modified skin substitute will enhance the allogeneic response to the IL-12-expressing cells in the skin substitute, which will help to ensure the efficient clearance of these cells. It is expected that the allogeneic immune response to the cells may promote additional infiltration of NK and CTL into the local tumor environment, and thereby augment the anti-tumor immune response. In some embodiments, the skin substitute persists in areas of tumor resection for a limited period, during which time the skin substitute provides a continuous local source of IL-12 to suppress tumor growth. In some embodiments, the present invention contemplates multiple applications of the skin substitute to sustain IL-12 secretion long enough to promote tumor regression. Resection of skin cancers by standard surgical excision or by Mohs' surgery generates an open wound that in many cases is left to heal by secondary intention [47]. The skin substitutes of the present invention provide sustained, local delivery of IL-12 to stimulate an immune response against residual tumor cells, while providing immediate wound coverage and promoting the ultimate healing of the surgical wound. The ability of wound healing factors secreted by viable skin substitutes to promote the healing of surgical wounds provides a significant advantage over biodegradable microspheres and other methods to provide sustained local release of immunomodulatory cytokines I. IL-12 Expression In some embodiments, the present invention provides host cells (e.g., keratinocytes) and skin substitutes expressing exogenous Interleukin (IL) IL-12. In some embodiments, the IL-12 is human IL-12. In some embodiments, the IL-12 is at least 50%, 60%, 70%, 80%, 90%, 95%, or 99% identical to an IL-12 protein (e.g., SEQ ID NO:1, 2 or 3). In some embodiments, the IL-12 is encoded by a nucleic acid at least 50%, 60%, 70%, 80%, 90%, 95%, or 99% identical to an IL-12 nucleic acid sequence, e.g., SEQ ID NO:4, 5, or 6. In some embodiments, the IL-12 sequence encodes a protein having at least one activity that is the same as wild-type IL-12. In some embodiments, the IL-12 is a fusion of the p35 and p40 IL-12 subunits (e.g., SEQ ID NO:3 (protein) or SEQ ID NO:6 (nucleic acid)). In some embodiments, the host cells or skin substitutes express an amount of bioactive IL-12 which is capable of inducing the proliferation of the PHA-stimulated lymphoblasts. In some embodiments, the host cells or skin substitutes secrete the bioactive IL-12.

In certain embodiments, an IL-12 DNA sequence is cloned into a cloning vector. A regulatory sequence that can be linked to the IL-12 DNA sequence in an expression vector is a promoter that is operable in the host cell in which the IL-12 is to be expressed. In some preferred embodiments, the IL-12 nucleic acid sequence (e.g., SEQ ID NO: 6) encodes an IL-12 fusion protein (e.g., SEQ ID NO: 3). In some embodiments, the IL-12 nucleic acid sequence comprises SEQ ID NOs: 4 and 5 separated by an RES sequence. In further embodiments, the IL-12 nucleic acid sequences of SEQ ID NOs: 4 and 5 may be separated by "self-cleaving" 2A peptides, such as those found in the foot and mouth disease virus. Optionally, other regulatory sequences can be used herein, such as one or more of an enhancer sequence, an intron with functional splice donor and acceptor sites, a signal sequence for directing secretion of IL-12, a polyadenylation sequence, other transcription terminator sequences, insulator elements, and a sequence homologous to the host cell genome. Other sequences, such as origin of replication, can be added to the vector as well to optimize expression of the desired IL-12. Further, a selectable marker can be present in the expression vector for selection of the presence thereof in the transformed host cells.

In preferred embodiments, the IL-12 sequence is operably linked to a regulatory sequence that drives the expression of the polypeptide (e.g., a promoter). In preferred embodiments, the regulatory sequence is the involucrin promoter or the keratin-14 promoter. However, any promoter that would allow expression of IL-12 in a desired host can be used in the present invention. Other mammalian promoter sequences that can be used herein are those from mammalian viruses that are highly expressed and that have a broad host range. Examples include the SV40 early promoter, the Cytomegalovirus ("CMV") immediate early promoter, mouse mammary tumor virus long terminal repeat ("LTR") promoter, adenovirus major late promoter (Ad MLP), and Herpes Simplex Virus ("HSV") promoter. In addition, promoter sequences derived from non-viral genes, such as the murine metallothionein gene, ubiquitin and elongation factor alpha (EF-1a) are also useful herein. These promoters can further be either constitutive or regulated, such as those that can be induced with glucocorticoids in hormone-responsive cells.

The present invention contemplates keratinocytes and skin substitutes expressing IL-12, and compositions and methods for making such cells. In some embodiments, host cells are induced to express exogenous polypeptides through transfection with an expression vector containing DNA encoding the exogenous polypeptide. An expression vector containing IL-12 DNA can be produced by operably linking IL-12 to one or more regulatory sequences such that IL-12 is expressed from the resulting vector in a desired host. Cell transformation procedures suitable for use include, for example with mammalian cell systems, dextran-mediated transfection, calcium phosphate precipitation, polybrene-mediated transfection, protoplast fusion, electroporation, encapsulation of the exogenous polynucleotide in liposomes, and direct microinjection of the DNA into nuclei.

II. Methods of Generating Human Skin Substitutes

In some embodiments, the present invention provides methods of generating human tissues such as skin substitutes (e.g., from NIKS® cells) that express exogenous IL-12. In preferred embodiments, vectors designed for expression of exogenous IL-12 in a desired host cell are introduced into the host cell, and the host cell is used to make a skin substitute.

A) Host Cells

Generally, any source of cells or cell line that can stratify into squamous epithelia is useful in the present invention. Accordingly, the present invention is not limited to the use of any particular source of cells that are capable of differentiating into squamous epithelia. Indeed, the present invention contemplates the use of a variety of cell lines and sources that can differentiate into squamous epithelia, including both primary and immortalized keratinocytes. Sources of cells include keratinocytes and dermal fibroblasts biopsied from humans and cadaveric donors (Auger et al., In Vitro Cell. Dev. Biol.—Animal 36:96-103; U.S. Pat. Nos. 5,968,546 and 5,693,332, each of which is incorporated herein by reference), neonatal foreskins (Asbill et al., Pharm. Research 17(9): 1092-97 (2000); Meana et al., Burns 24:621-30 (1998); U.S. Pat. Nos. 4,485,096; 6,039,760; and 5,536,656, each of which is incorporated herein by reference), and immortalized keratinocytes cell lines such as NM1 cells (Baden, In Vitro Cell. Dev. Biol. 23(3):205-213 (1987)), HaCaT cells (Boucamp et al., J. cell. Boil. 106: 761-771 (1988)); and NIKS® cells (Cell line BC-1-Ep/SL; U.S. Pat. No. 5,989,837, incorporated herein by reference; ATCC CRL-12191). Each of these cell lines can be cultured or genetically modified as described below in order to produce a cell line capable of expressing an exogenous polypeptide such as IL-12.

In particularly preferred embodiments, NIKS® cells or cells derived from NIKS® cells are utilized. (Cell line BC-1-Ep/SL; U.S. Pat. Nos. 5,989,837, 6,514,711, 6,495, 135, 6,485,724, and 6,214,567; each of which is incorporated herein by reference; ATCC CRL-12191). The discovery of a novel human keratinocyte progenitor cell line (near-diploid immortalized keratinocytes or NIKS®) provides an opportunity to genetically modify human keratinocytes for new therapeutic methods. The NIKS® keratinocyte cell line, identified and characterized at the University of Wisconsin, is nontumorigenic, exhibits a stable karyotype, and undergoes normal differentiation both in monolayer and organotypic culture. NIKS® cells form fully stratified skin substitutes in organotypic culture. These cultures are indistinguishable by all criteria tested thus far from organotypic cultures formed from primary human keratinocytes. Unlike primary cells however, the immortalized NIKS® cells will continue to proliferate indefinitely in monolayer culture. This provides an opportunity to genetically manipulate the cells and isolate clones of cells with new useful properties (Allen-Hoffmann et al., J. Invest. Dermatol., 114(3): 444-455 (2000)).

The NIKS® cells arose from the BC-1-Ep strain of human neonatal foreskin keratinocytes isolated from an apparently normal male infant. In early passages, the BC-1-Ep cells exhibited morphological and growth characteristics that were typical of cultured normal human keratinocytes. Cultivated BC-1-Ep cells exhibited stratification as well as features of programmed cell death. To determine replicative lifespan, the BC-1-Ep cells were serially cultivated to senescence in standard keratinocyte growth medium at a density of $3 \times 10^5$ cells per 100-mm dish and passaged at weekly intervals (approximately a 1:25 split). By passage 15, most keratinocytes in the population appeared senescent as judged by the presence of numerous abortive colonies that contained large, flat cells. However, at passage 16, keratinocytes exhibiting a small cell size were evident in one culture dish. By passage 17, only the small-sized keratinocytes were present in the culture and no large, senescent keratinocytes were evident. The resulting population of small keratinocytes that survived this putative crisis period appeared morphologically uniform and produced colonies of keratinocytes exhibiting typical keratinocyte characteristics including cell-cell adhesion and apparent squame production. The keratinocytes that escaped senescence were serially cultivated at weekly intervals at a density of $3 \times 10^5$ cells per 100-mm dish. Typically the cultures reached a cell density of approximately $8 \times 10^6$ cells within 7 days. This stable rate of cell growth was maintained through at least 59 passages, demonstrating that the cells had achieved immortality. The keratinocytes that emerged from the original senescent population were originally designated BC-1-Ep/Spontaneous Line and are now termed NIKS®. The NIKS® cell line has been screened for the presence of DNA sequences for HIV-1, HIV-2, EBV, CMV, HTLV-1, HTLV-2, HBV, HCV, HHV-6, HHV-7, SV40, B-19 parvovirus, HPV-16, HPV-18, and HPV-31 using either PCR or Southern analysis. None of these viruses were detected.

Cytogenetic analysis was performed on the parental BC-1-Ep cells at passage 3 and NIKS® cells at passages 31 and 54. The parental BC-1-Ep cells had a normal chromosomal complement of 46, XY. At passage 31, all NIKS® cells contained 47 chromosomes with an extra isochromosome of the long arm of chromosome 8. No other gross chromosomal abnormalities or marker chromosomes were detected. At passage 54, all cells contained the isochromosome 8.

The DNA fingerprints for the NIKS® cell line and the BC-1-Ep keratinocytes are identical at all twelve loci analyzed demonstrating that the NIKS® cells arose from the parental BC-1-Ep population. The odds of the NIKS® cell line having the parental BC-1-Ep DNA fingerprint by random chance is 4×10-16. The DNA fingerprints from three different sources of human keratinocytes, ED-1-Ep, SCC4 and SCC13y are different from the BC-1-Ep pattern. This data also shows that keratinocytes isolated from other humans, ED-1-Ep, SCC4, and SCC13y, are unrelated to the BC-1-Ep cells or each other. The NIKS® DNA fingerprint data provides an unequivocal way to identify the NIKS® cell line.

Loss of p53 function is associated with an enhanced proliferative potential and increased frequency of immortality in cultured cells. The sequence of p53 in the NIKS® cells is identical to published p53 sequences (GenBank accession number: M14695). In humans, p53 exists in two predominant polymorphic forms distinguished by the amino acid at codon 72. Both alleles of p53 in the NIKS® cells are wild type and have the sequence CGC at codon 72, which codes for an arginine. The other common form of p53 has a proline at this position. The entire sequence of p53 in the NIKS® cells is identical to the BC-1-Ep progenitor cells. Rb was also found to be wild type in NIKS® cells.

Anchorage-independent growth is highly correlated to tumorigenicity in vivo. For this reason, the anchorage-independent growth characteristics of NIKS® cells in agar or methylcellulose-containing medium was investigated. After 4 or 8 weeks in either agar- or methylcellulose-containing medium, NIKS® cells remained as single cells.

Cells were injected into the flanks of athymic nude mice to determine the tumorigenicity of the parental BC-1-Ep keratinocytes and the immortal NIKS® keratinocyte cell line. The human squamous cell carcinoma cell line, SCC4, was used as a positive control for tumor production in these animals. The injection of samples was designed such that animals received SCC4 cells in one flank and either the parental BC-1-Ep keratinocytes or the NIKS® cells in the opposite flank. This injection strategy eliminated animal to animal variation in tumor production and confirmed that the mice would support vigorous growth of tumorigenic cells. Neither the parental BC-1-Ep keratinocytes (passage 6) nor the NIKS® keratinocytes (passage 35) produced tumors in athymic nude mice.

NIKS® cells were analyzed for the ability to undergo differentiation in both surface culture and organotypic culture. For cells in surface culture, the formation cornified envelopes was monitored as a marker of squamous differentiation. In cultured human keratinocytes, early stages of cornified envelope assembly result in the formation of an immature structure composed of involucrin, cystatin-α, and other proteins, which represent the innermost third of the mature cornified envelope. Less than 2% of the keratinocytes from the adherent BC-1-Ep cells or the NIKS® cell line produce cornified envelopes. This finding is consistent with previous studies demonstrating that actively growing, subconfluent keratinocytes produce less than 5% cornified envelopes. To determine whether the NIKS® cell line is capable of producing cornified envelopes when induced to differentiate, the cells were removed from surface culture and suspended for 24 hours in medium made semi-solid with methylcellulose. Many aspects of terminal differentiation, including differential expression of keratins and cornified envelope formation can be triggered in vitro by loss of keratinocyte cell-cell and cell-substratum adhesion. The NIKS® keratinocytes produced as many as and usually more cornified envelopes than the parental keratinocytes. These findings demonstrate that the NIKS® keratinocytes are not defective in their ability to initiate the formation of this cell type-specific differentiation structure.

To confirm that the NIKS® keratinocytes can undergo squamous differentiation, the cells were cultivated in organotypic culture. Keratinocyte cultures grown on plastic substrata and submerged in medium replicate but exhibit limited differentiation. Specifically, human keratinocytes become confluent and undergo limited stratification producing a sheet consisting of 3 or more layers of keratinocytes. By light and electron microscopy there are striking differences between the architecture of the multilayered sheets formed in tissue culture and intact human skin. In contrast, organotypic culturing techniques allow for keratinocyte growth and differentiation under in vivo-like conditions. Specifically, the cells adhere to a physiological substratum consisting of dermal fibroblasts embedded within a fibrillar collagen base. The organotypic culture is maintained at the air-medium interface. In this way, cells in the upper sheets are air-exposed while the proliferating basal cells remain closest to the gradient of nutrients provided by diffusion through the collagen gel. Under these conditions, correct tissue architecture is formed. Several characteristics of a normal differentiating epidermis are evident. In both the parental cells and the NIKS® cell line a single layer of cuboidal basal cells rests at the junction of the epidermis and the dermal equivalent. The rounded morphology and high nuclear to cytoplasmic ratio is indicative of an actively dividing population of keratinocytes. In normal human epidermis, as the basal cells divide they give rise to daughter cells that migrate upwards into the differentiating layers of the tissue. The daughter cells increase in size and become flattened and squamous. Eventually these cells enucleate and form cornified, keratinized structures. This normal differentiation process is evident in the upper layers of organotypic cultures prepared from both the parental cells and the NIKS® cells. The appearance of flattened squamous cells is evident in the upper layers of the organotypic cultures and demonstrates that stratification has occurred. In the uppermost part of the organotypic cultures the enucleated squames peel off the top of the culture. To date, no histological differences in differentiation at the light microscope level between the parental keratinocytes and the NIKS® keratinocyte cell line grown in organotypic culture have been observed.

To observe more detailed characteristics of the parental (passage 5) and NIKS® (passage 38) organotypic cultures and to confirm the histological observations, samples were analyzed using electron microscopy. Organotypic cultures of the parental cells and the NIKS® cells were harvested after 15 days and sectioned perpendicular to the basal layer to show the extent of stratification. Both the parental cells and the NIKS® cell line undergo extensive stratification in organotypic culture and form structures that are characteristic of normal human epidermis. Abundant desmosomes are formed in organotypic cultures of parental cells and the NIKS® cell line. The formation of a basal lamina and associated hemidesmosomes in the basal keratinocyte layers of both the parental cells and the cell line was also noted.

Hemidesmosomes are specialized structures that increase adhesion of the keratinocytes to the basal lamina and help maintain the integrity and strength of the tissue. The presence of these structures was especially evident in areas where the parental cells or the NIKS® cells had attached directly to the porous support. These findings are consistent with earlier ultrastructural findings using human foreskin keratinocytes cultured on a fibroblast-containing porous support. Analysis at both the light and electron microscopic levels demonstrate that the NIKS® cell line in organotypic culture can stratify, differentiate, and form structures such as desmosomes, basal lamina, and hemidesmosomes found in normal human epidermis.

In some embodiments, the present invention provides host cells, such as NIKS® cells, that are stably transfected or transiently transfected with a vector construct that allows expression of exogenous IL-12 in the host cell. In some preferred embodiments, the host cells that express exogenous IL-12 are used to make skin substitutes. In some embodiments, organotypic culturing techniques allow for keratinocyte growth and differentiation under in vivo-like conditions. In some embodiments, the host cells adhere to a physiological substratum (a dermal equivalent) comprising dermal fibroblasts embedded within a fibrillar collagen base. In some embodiments, the organotypic culture is maintained at the air-medium interface. In some preferred embodiments, the skin substitutes have correct tissue architecture, including, but not limited to, stratified squamous epithelia and the other hallmarks described above.

The present invention is not limited to the production of skin substitutes by the methods described here. Indeed, a variety of organotypic culture techniques may be used to produce skin substitutes, including those described in U.S. Pat. Nos. 5,536,656 and 4,485,096, both of which are incorporated herein by reference. In some embodiments, different populations of keratinocytes are used to construct the skin substitute. Accordingly, in some embodiments, the skin substitutes of the present invention are formed from keratinocytes derived from an immortalized cell line (e.g., NIKS® cells) and cells derived from a patient. In other embodiments, the skin substitutes of the present invention are formed from at least a first population of keratinocytes derived from an immortalized cell line that express IL-12 and a second population of keratinocytes derived from an immortalized cell line that do not express an exogenous polypeptide. It is contemplated that by varying the ratio of the two populations the dose of IL-12 delivered can be varied. In still other embodiments, the skin substitutes are formed from at least a first population of keratinocytes expressing IL-12, at least a second population of keratinocytes expressing a second exogenous polypeptide, and/or keratinocytes derived from a patient.

III. Treatment of Skin Cancer with Keratinocytes Transfected with Exogenous IL-12

In some embodiments, the present invention contemplates treatment of skin cancer or a site where a skin cancer has been removed (resection site) with keratinocytes and/or skin substitutes expressing exogenous IL-12. In some embodiments, cells expressing IL-12 are topically applied to wound sites. In some embodiments, the keratinocytes are applied via a spray, while in other embodiments, the keratinocytes are applied via a gel. In other embodiments, cells expressing IL-12 are used for engraftment on resection sites.

IV. Testing Methods

The host cells and skin substitutes of the present invention may be used for a variety of in vitro tests. In particular, the host cells and skin substitutes find use in the evaluation of: skin care products, drug metabolism, cellular responses to test compounds, wound healing, phototoxicity, dermal irritation, dermal inflammation, skin corrosivity, and cell damage. The host cells and skin substitutes are provided in a variety of formats for testing, including 6-well, 24-well, and 96-well plates. Additionally, the skin substitutes can be divided by standard dissection techniques and then tested. The skin substitutes of the present invention may have both an epidermal layer with a differentiated stratum corneum and dermal layer that includes dermal fibroblasts.

The present invention encompasses a variety of screening assays. In some embodiments, the screening method comprises providing a host cell or skin substitutes of the present invention and at least one test compound or product (e.g., a skin care product such as a moisturizer, cosmetic, dye, or fragrance; the products can be in any from, including, but not limited to, creams, lotions, liquids and sprays), applying the product or test compound to the host cell or skin substitute, and assaying the effect of the product or test compound on the host cell or skin substitute. A wide variety of assays are used to determine the effect of the product or test compound on the skin substitute. These assays include, but are not limited to, MTT cytotoxicity assays (Gay, The Living Skin Equivalent as an In Vitro Model for Ranking the Toxic Potential of Dermal Irritants, Toxic. In Vitro (1992)) and ELISA to assay the release of inflammatory modulators (e.g., prostaglandin E2, prostacyclin, and interleukin-1-alpha) and chemoattractants. The assays can be further directed to the toxicity, potency, or efficacy of the compound or product. Additionally, the effect of the compound or product on growth, barrier function, or tissue strength can be tested.

In particular, the present invention contemplates the use of host cells or skin substitutes for high throughput screening of compounds from combinatorial libraries (e.g., libraries containing greater than 104 compounds). In some embodiments, the cells are used in second messenger assays that monitor signal transduction following activation of cell-surface receptors. In other embodiments, the cells can be used in reporter gene assays that monitor cellular responses at the transcription/translation level. In still further embodiments, the cells can be used in cell proliferation assays to monitor the overall growth/no growth response of cells to external stimuli.

In second messenger assays, host cells or skin substitute is treated with a compound or plurality of compounds (e.g., from a combinatorial library) and assayed for the presence or absence of a second messenger response. In some preferred embodiments, the cells (e.g., NIKS® cells) used to create skin substitutes are transfected with an expression vector encoding a recombinant cell surface receptor, ion-channel, voltage gated channel or some other protein of interest involved in a signaling cascade. It is contemplated that at least some of the compounds in the combinatorial library can serve as agonists, antagonists, activators, or inhibitors of the protein or proteins encoded by the vectors. It is also contemplated that at least some of the compounds in the combinatorial library can serve as agonists, antagonists, activators, or inhibitors of protein acting upstream or downstream of the protein encoded by the vector in a signal transduction pathway.

In some embodiments, the second messenger assays measure fluorescent signals from reporter molecules that respond to intracellular changes (e.g., Ca2+ concentration, membrane potential, pH, IP3, cAMP, arachidonic acid release) due to stimulation of membrane receptors and ion channels (e.g., ligand gated ion channels; see Denyer et al., Drug Discov. Today 3:323-32 [1998]; and Gonzales et al., Drug. Discov. Today 4:431-39 [1999]). Examples of reporter molecules include, but are not limited to, FRET (florescence resonance energy transfer) systems (e.g., Cuo-lipids and oxonols, EDAN/DABCYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the cells comprising skin substitutes are loaded with the indicator prior to exposure to the compound. Responses of the host cells to treatment with the compounds can be detected by methods known in the art, including, but not limited to, fluorescence microscopy, confocal microscopy (e.g., FCS systems), flow cytometry, microfluidic devices, FLIPR systems (See, e.g., Schroeder and Neagle, J. Biomol. Screening 1:75-80 [1996]), and plate-reading systems. In some preferred embodiments, the response (e.g., increase in fluorescent intensity) caused by compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

The host cells and skin substitutes of the present invention are also useful in reporter gene assays. Reporter gene assays involve the use of host cells transfected with vectors encoding a nucleic acid comprising transcriptional control elements of a target gene (i.e., a gene that controls the biological expression and function of a disease target or inflammatory response) spliced to a coding sequence for a reporter gene. Therefore, activation of the target gene results in activation of the reporter gene product. This serves as indicator of response such an inflammatory response. Therefore, in some embodiments, the reporter gene construct comprises the 5' regulatory region (e.g., promoters and/or enhancers) of a protein that is induced due to skin inflammation or irritation or protein that is involved in the synthesis of compounds produced in response to inflammation or irritation (e.g., prostaglandin or prostacyclin) operably linked to a reporter gene. Examples of reporter genes finding use in the present invention include, but are not limited to, chloramphenicol transferase, alkaline phosphatase, firefly and bacterial luciferases, β-galactosidase, β-lactamase, and green fluorescent protein. The production of these proteins, with the exception of green fluorescent protein, is detected through the use of chemiluminescent, colorimetric, or bioluminecent products of specific substrates (e.g., X-gal and luciferin). Comparisons between compounds of known and unknown activities may be conducted as described above.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); pmol (micromoles); nmol (nanomoles); g (grams); mg (milligrams); μg (micrograms); ng (nanograms); I or L (liters); ml (milliliters); μl (microliters); cm (centimeters); mm (millimeters); μm (micrometers); nm (nanometers); ° C. (degrees Centigrade); U (units), mU (milliunits); min. (minutes); sec. (seconds); % (percent); kb (kilobase); by (base pair); PCR (polymerase chain reaction); BSA (bovine serum albumin).

Example 1: NIKS® Skin Substitutes do not Express Detectable Levels of IL-12

Several groups have reported expression of IL-12 in cultured human keratinocytes as detected by sensitive nested RT-RCR methods [52-54]. However, analysis of IL-12 expression in organotypic skin cultures has not been reported. To determine the baseline level of IL-12 produced by skin substitutes prepared from NIKS® cells, a commercially-available IL-12 ELISA kit (R&D Systems, Minneapolis, Minn.) was used to quantify IL-12 in conditioned medium. Although the standard curve for the ELISA conformed to the kit validity criteria, IL-12 was not detected in conditioned medium at levels above the lowest IL-12 standard (31 pg/ml). These results demonstrate that skin substitute tissue prepared from NIKS® keratinocytes expresses little, if any IL-12.

Example 2: IL-12 Vector Design and Construction

IL-12 is a heterodimer consisting of disulfide linked p40 and p35 subunits. Because the p40 subunit can form homodimers that are antagonistic to IL-12 bioactivity, it is important to avoid excess p40 production that could lead to the production of inhibitory p40 homodimers. To ensure expression of biologically active IL-12, the p40 and p35 subunits have been expressed as a fusion protein (p40/p35) with the two separated by a short, flexible linker (Gly6Ser). Lieschke et al. demonstrated that this p40/p35 fusion protein exhibited bioactivity comparable to recombinant human IL-12 (Lieschke et al., Nat Biotechnol., 15(1): 35-40 (1997)). This approach was shown to produce more bioactive IL-12 than co-transfection of cells with separate p35 and p40 expression constructs or bicistronic expression constructs where p35 and p40 were linked by an IRES.

The strategy for production of the DNA fragment encoding the p40/p35 fusion protein is shown in FIG. 5. Initially, the IL-12 p40 and p35 subunits were amplified separately from mRNA isolated from THP-1 cells stimulated with phorbol 12-myristate 13-acetate, lipopolysaccharide, and interferon-γ by PCR. The p40 forward primer has been designed to retain the translation initiation site and secretory leader sequences. The p40 reverse primer encompasses the last 21 nucleotides of the p40 coding sequence, followed in frame by the Gly6Ser linker and the first 10 nucleotides of the p35 subunit downstream from the p35 leader sequence. The p35 forward primer encodes the last 10 nucleotides of the p40 coding region fused in frame to the Gly6Ser linker followed by 21 nucleotides of the p35 coding region beginning with the first amino acid following the 22 amino acid p35 leader sequence. The p35 reverse primer encompasses the translational stop codon. The separately amplified p40 and p35 products were denatured and annealed using the overlapping Gly6Ser linker sequences in each cDNA. The final fusion cDNA was amplified by PCR with the p40 forward primer and p35 reverse primers. Primers contain restriction enzyme sites to permit cloning of the p40/p35 fusion construct into the final expression vectors.

The fragment encoding the IL-12 p40/p35 fusion protein has been cloned into non-viral plasmid expression vectors downstream from the human keratinocyte-specific involucrin (INV) and keratin 14 (K14) promoters. These vectors also contain a selection cassette that confers resistance to blasticidin in stably-transfected cells. The integrity of the final expression constructs will be determined by sequencing and restriction enzyme analysis.

Figure 6A:
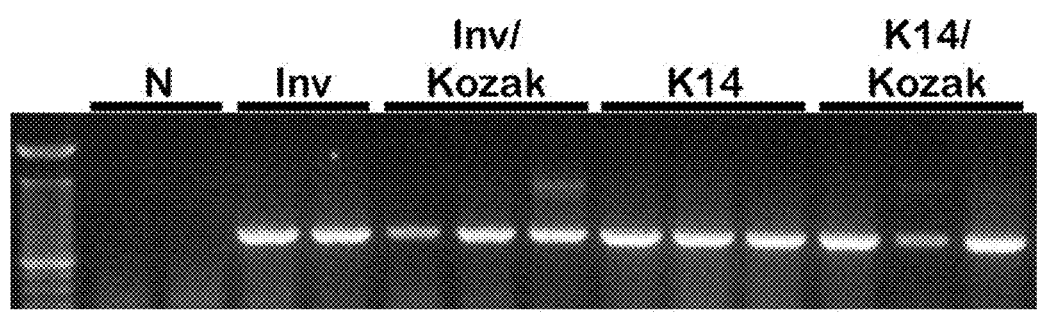
FIG. 6A and FIG. 6B show the IL-12 mRNA expression levels by RT-PCR and protein levels by ELISA, respectively, after transient transfection of the expression vectors into NIKS® cells.
Figure 6B:
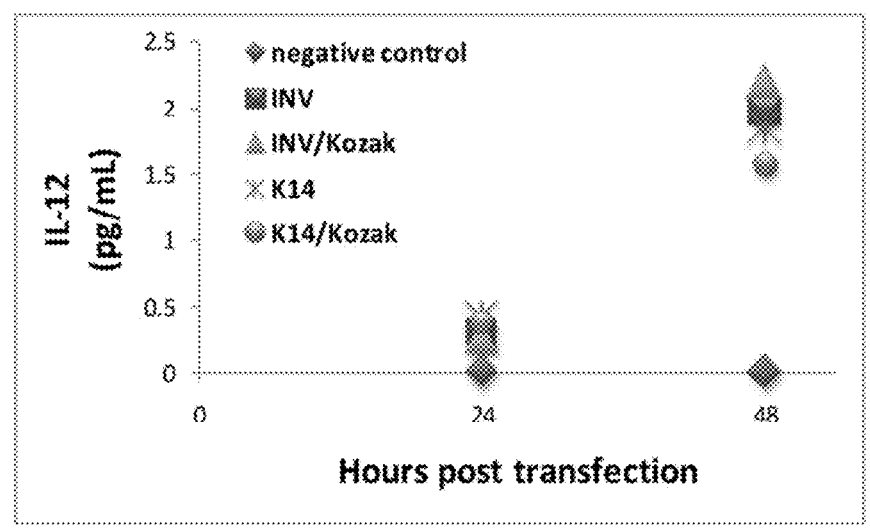

Example 3: Transient Transfection of NIKS® Cells in Monolayer Culture and Evaluation of IL-12 Fusion mRNA Levels Expression of the IL-12 fusion protein have been evaluated initially in transiently-transfected cells. NIKS® cells were transfected with the IL-12 expression constructs or empty expression vectors. All transfected cultures were assayed for mRNA expression levels approximately 24 hrs post-transfection to verify transgene expression. Total RNA was isolated with Trizol (Invitrogen, Carlsbad Calif.) and treated with DNAse to eliminate residual transfected vector DNA. RT-PCR was performed using primers that specifically amplify the IL-12 p40/p35 RNA transcribed from the expression constructs, but not endogenous IL-12 mRNA. The primers were designed to span an intron in the rabbit β-globin fragment in the vector such that products derived from mRNA are easily distinguished from products resulting from amplification of residual vector DNA. Culture medium from cells transiently-transfected with the IL-12 fusion transgene was assayed for IL-12 fusion protein production using a commercially-available ELISA kit (R&D Systems). As indicated in Example 1 and FIG. 6, unmodified NIKS® cells do not express IL-12 at levels detectable by ELISA whereas cells transiently-transfected with the IL-12 expression vectors exhibit detectable RT-PCR product of the correct size (FIG. 6A). Culture medium collected from transiently transfected samples after 24 and 48 hours showed that IL-12 was not detectable in media from untransfected cells, however, IL-12 was readily detected in cells transiently transfected with each of the IL-12 expression constructs, with higher levels of expression observed after 48 hours (FIG. 6B).

Example 4: Isolation and Characterization of Clones of Stably-Transfected NIKS® Cells Expressing Elevated Levels of IL-12 (NIKS$^{IL-12}$)

Individual clones of NIKS® cells stably transfected with the IL-12 fusion expression vectors have been isolated and characterized. These clones were analyzed for IL-12 transgene expression, ability to form a properly stratified skin substitute, and total IL-12 protein expression (ELISA). Using these assays, stably-transfected clones will be ranked according to levels of bioactive IL-12 fusion protein produced.

Selection of Stable Transfectants.

We generated a panel of clonally-derived NIKS® cells that are stably transfected with the IL-12 vectors. NIKS® cells were transfected by electroporation and plated at clonal density on a feeder layer of murine 3T3 cells. One day after plating, cells were switched to keratinocyte medium containing blasticidin. Clones that have stably incorporated the expression vectors were recovered after three weeks of blasticidin selection. Forty-five colonies (NIKS$^{IL-12}$) were picked to individual culture dishes, expanded, and cryopreserved. Each clone was counted at each passage to determine growth rate and ability to be maintained in an undifferentiated state. Clones that exhibited alterations in cell morphology or growth rates more than 25% higher or lower than untransfected NIKS® cells were excluded from further characterization.

Analysis of Transgene Expression.

RT-PCR was used to screen 45 selected colonies for expression of the IL-12 p40/p35 expression construct. Based on the results of the RT-PCR screening, 13 clones were selected for further characterization (FIG. 10). Cryopreserved cells were thawed, cultured, and assessed for growth rates and IL-12 secretion was determined by ELISA (FIG. 10). These results showed NIKS$^{IL-12}$ clones expressing a broad range of IL-12 levels which remained stable over serial passes.

Clones were ranked according to the strength of transgene expression. Because it is not possible to predict the optimal level of IL-12 expression, we selected 13 clones that encompass a broad range of transgene expression levels for further analysis.

Preparation and Characterization of Organotypic Cultures.

Figure 7A:
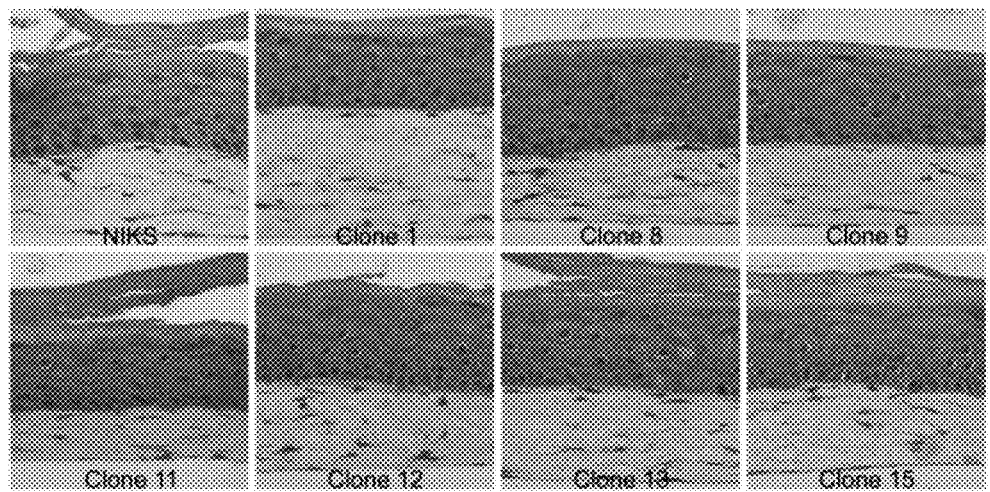
FIG. 7A, FIG. 7B, and FIG. 7C show the tissue structure of the skin tissues generated using the NIKS$^{IL-12}$ clones by hematoxylin and eosin staining, the cell viability of these tissues, and the barrier function of these skin tissues, respectively.
Figure 7B:
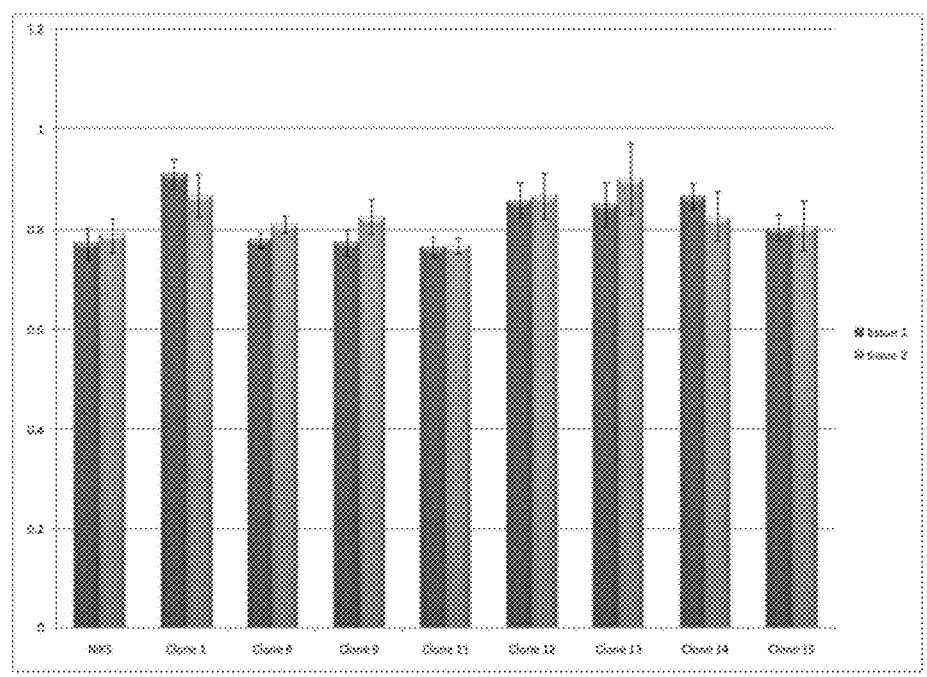
Figure 7C:
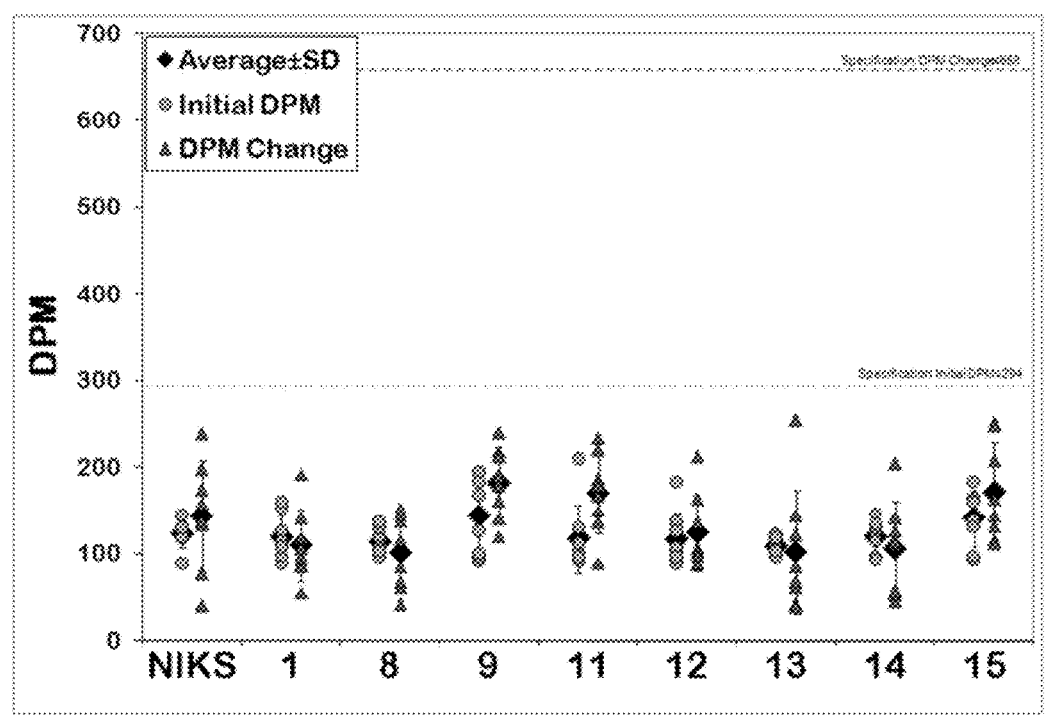

The clones identified above were further characterized under organotypic culturing conditions to generate stratified skin substitute tissues and analyzed for tissue structure and function as well as IL-12 expression and localization. Briefly, stably-transfected NIKS$^{IL-12}$ clones were seeded onto the surface of dermal equivalents composed of viable human dermal fibroblasts embedded in a gelled matrix of type I collagen. The tissues were lifted to the air-medium interface after 5 days and maintained in air-exposed culture for 14 days to promote epidermal stratification. At the end of this period, NIKS® cells form mature skin substitute tissue. Tissues were analyzed using a panel of quality control assays. Histological sections were fixed and stained with hematoxylin and eosin (H&E) to assess the extent and quality of the tissue architecture for clinical acceptance criteria based on those for StrataGraft® tissue. This assessment includes evaluation of: clearly distinguishable dermal and epidermal compartments, a dermal compartment containing fibroblasts, a layer of small nucleated keratinocytes at the dermal-epidermal junction, several layers of differentiating keratinocytes above the basal layer, and flattened corneocytes close to the top of the tissue section. The NIKS$^{IL-12}$ tissues exhibit appropriate differentiation in the epidermal compartment, including the presence of basal, squamous, granular, and cornified tissue layers (FIG. 7A). Tissue viability and metabolic activity was assessed by incubation for 90 minutes in culture medium containing 1 mg/ml 3-[4,5-dimethylthiazol-2-yl]-2,5-diphenyltetrazolium bromide (MTT). The amount of MTT that is metabolized to its formazan product was quantified by measuring the absorbance of the extracted MTT-formazan product at 550 nm. The NIKS$^{IL-12}$ tissues possess viability comparable to that for unmodified NIKS® tissues (FIG. 7B). Epidermal barrier function was assessed by measuring changes in the impedance of the skin surface with a NOVA DPM9003 impedance meter. The magnitude of the change in impedance readings during a defined measurement interval is proportional to the rate of water flux across the epidermal permeability barrier of the stratum corneum. These data show the NIKS$^{IL-12}$ tissues possess barrier function comparable to that for unmodified NIKS® tissues (FIG. 7C).

Evaluation of Exogenous IL-12 Fusion Protein Secretion.

Figure 8A:
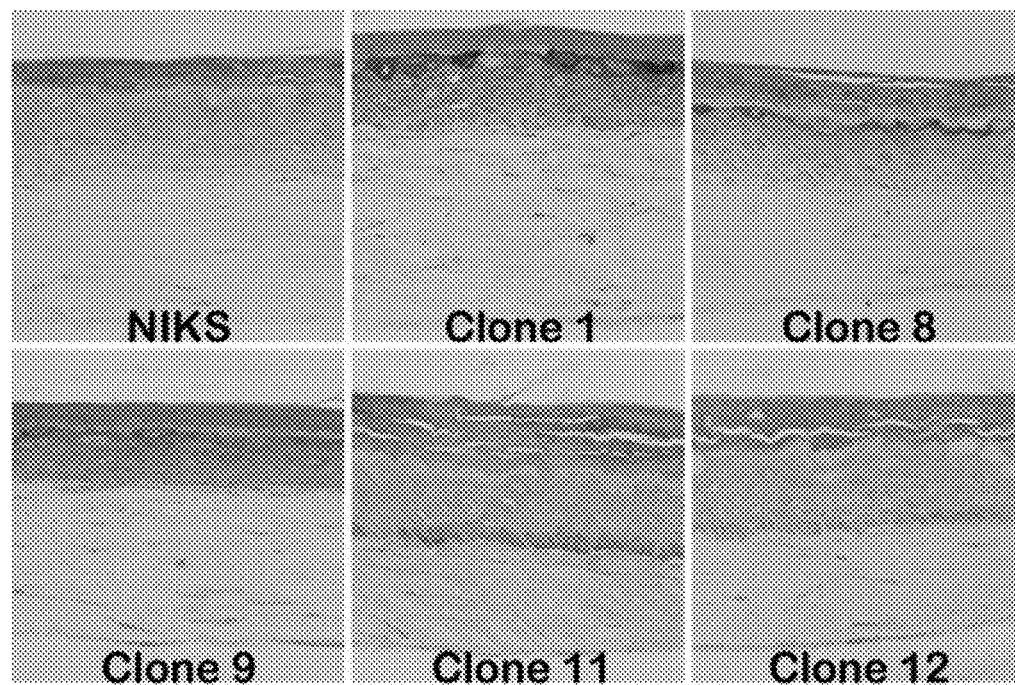
FIG. 8A, FIG. 8B, and FIG. 8C show the localization of the IL-12 within the tissues by immunohistochemistry, the amount of IL-12 present in the media conditioned by the tissues, and the immunoblot analysis of the IL-12 within the tissues, respectively.
Figure 8B:
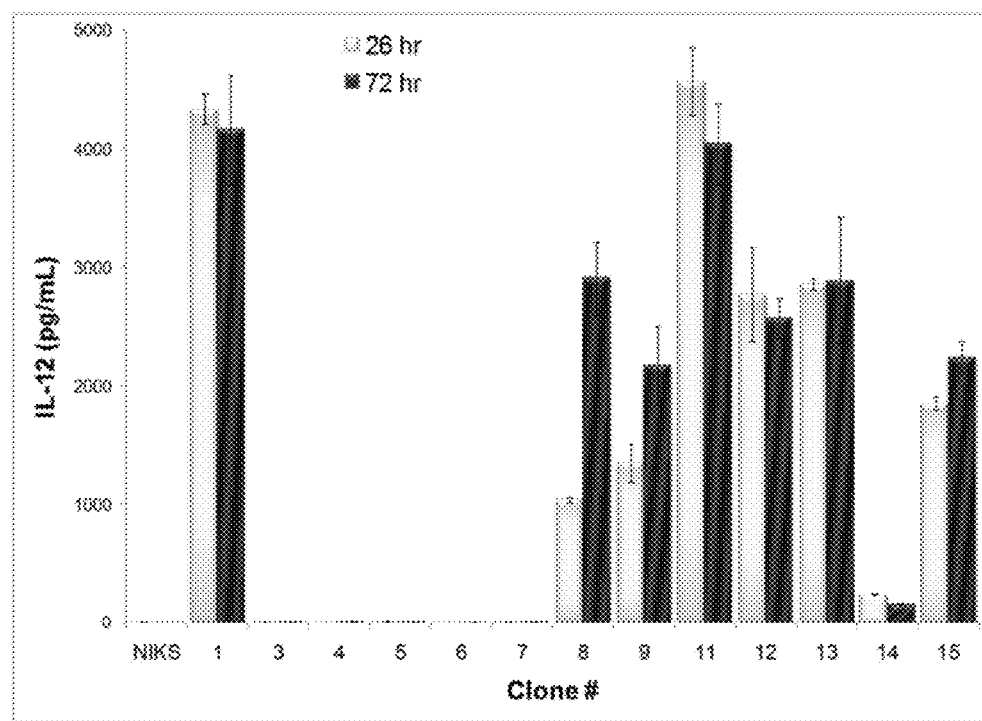
Figure 8C:
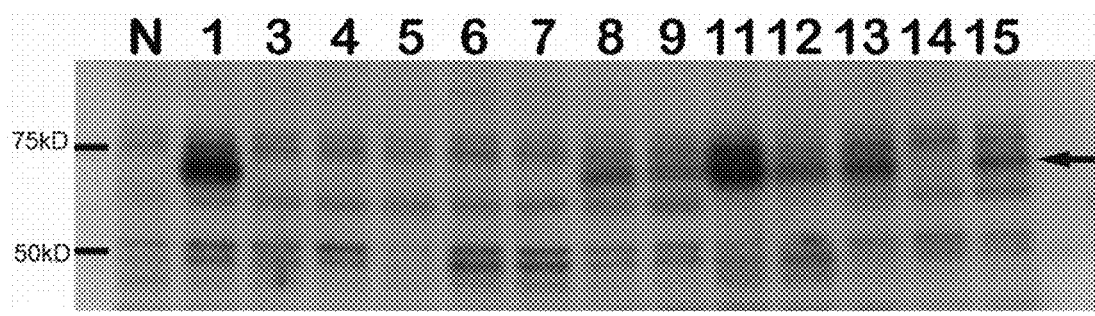

To compare the levels of IL-12 produced by the NIKS$^{IL-12}$ clones, mature organotypic skin cultures were allowed to secrete IL-12 into culture media for 24 or 48 hours. The amount of IL-12 in conditioned media from each clone was quantified by an ELISA specific for IL-12. As shown in Example 1, unmodified NIKS® tissue does not produce IL-12 at levels detectable by ELISA. Tissue localization of the IL-12 protein within the tissues was assessed by immunohistochemistry. FIG. 8A shows tissue-appropriate IL-12 localization based on the construct promoter. Clones 1, 8, and 9 show staining in the upper, more differentiated cell layers of the epidermis as would be expected for protein expression driven by the involucrin promoter. Involucrin is not expressed by basal cells but is expressed once keratinocytes begin to terminally differentiate. In contrast, Clones 11 and 12 show expression in the basal cell layer which is consistent with expression driven by the K14 promoter. As a result of the extensive crosslinking which occurs in the upper layers of the epidermal compartment, one might predict that protein expressed in the lower layers of the epidermal compartment would be more readily available to diffuse across the dermis and into the media below the tissues. It is possible therefore, that the lighter staining seen in the tissues generated from NIKS$^{IL-12}$ clones expressing IL-12 under the control of the K14/Kozak promoter, is due to increased relative diffusion of the IL-12 from the lower epidermal layers to the media below. Samples of the tissues were also analyzed by immunoblot using an IL-12 specific antibody (R&D Systems) under denaturing conditions to confirm that the IL-12 p40/p35 subunits are expressed as a fusion protein instead of a disulfide-linked heterodimer. FIG. 8C shows that the relative intensity of the IL-12 band by immunoblot mimics the levels seen by ELISA and that the apparent molecular weight of the IL-12 is consistent with that of the fusion protein.

Figure 9:
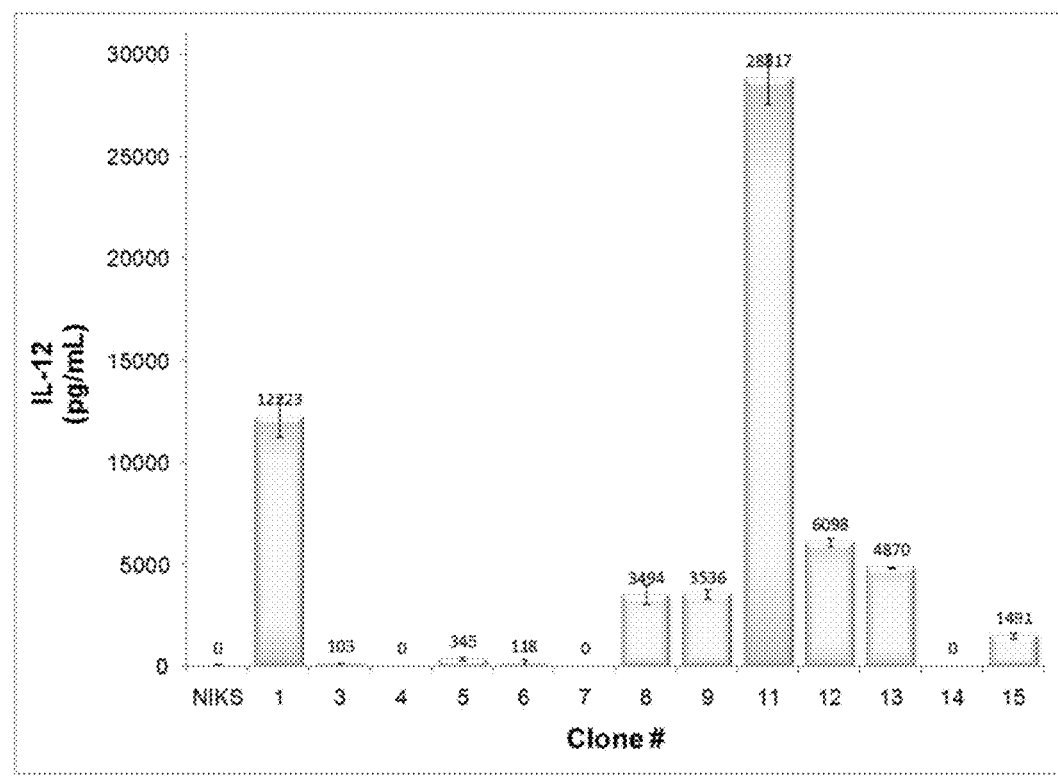
FIG. 9 is a graph of bioactivity of the IL-12 in the conditioned media from the NIKS cells and NIKS$^{IL-12}$ clones based on proliferation of human PHA-activated lymphoblasts.

Example 5: Demonstration of Secretion of Bioactive IL-12 From Organotypic Skin Tissue Prepared from Stably-Transfected NIKS$^{IL-12}$ Clones The bioactivity of the IL-12 fusion protein secreted by NIKS$^{IL-12}$ clones was evaluated using an IL-12 capture bioassay that measures the ability of human IL-12 to stimulate the proliferation of phytohemagglutinin (PHA)-activated human lymphoblasts (Gately et al., Curr Protoc Immunol, Chapter 6: Unit 6 p. 16 (2001)). Human peripheral blood mononuclear cells (PBMC) were isolated from peripheral blood of healthy consented volunteers by Ficoll-Hypaque gradient centrifugation. PBMC were seeded at $5 \times 10^5$/ml in culture medium [1:1 RPMI:complete DMEM supplemented with 10 mM HEPES, 0.006% L-arginine HCl, 0.1% dextrose, and 5% human AB serum (Irvine Scientific)]. PHA-P was added to 10 µg/ml and cells incubated for 3 days at 37° C., 5% CO2. Cells were then diluted 2-fold with fresh medium containing 50 U/ml IL-2 and incubated for 24 hr to promote lymphoblast proliferation. PHA-activated lymphoblasts were collected by centrifugation, rinsed in culture medium to remove PHA and IL-2, counted with trypan blue to determine the number of viable cells, and suspended at $2 \times 10^5$ cells per ml. 96-well plates were coated with a non-neutralizing anti-human IL-12 capture antibody (R&D Systems) overnight at 4° C. Plates were then washed and dilutions of known concentrations of recombinant human IL-12 (R&D Systems) or conditioned medium from the skin tissues generated from unmodified NIKS or the NIKS$^{IL-12}$ clones were captured by the antibody bound onto the plates. Unbound sample was then washed out and $2 \times 10^4$ PHA-activated human lymphoblasts were added to each well. Plates were incubated for 2 days to allow captured IL-12 to stimulate the proliferation of the PHA-activated lymphocytes. Proliferative cells were quantified by incorporation of 3H-thymidine during the last 18 hours of the culture period and the amount of IL-12 bioactivity in conditioned medium from NIKS$^{IL-12}$ clones was determined from a standard curve generated using a rhIL-12 standard. FIG. 9 shows that the skin substitute tissues generated from the NIKS$^{IL-12}$ clones generates significant amounts of bioactive IL-12 which is capable of inducing the proliferation of the PHA-stimulated lymphoblasts.

Example 6: Characterization of NIKS$^{IL-12}$ Clones for Tumorigenicity, Karyotype, and Transgene Configuration Analysis of Transgene Integration Site and Copy Number.

Genomic DNA from the three most promising clones identified above will be characterized for site(s) of transgene integration and copy number. As required by the FDA, this analysis will be repeated prior to clinical evaluation to ensure that the genomic configuration of the transgene is maintained during cGMP cell banking Stable cell lines will be characterized by Southern blot analysis using digoxygenin-labeled probes derived from the IL-12 expression vectors. Southern blot results will reveal transgene copy number and number of integration sites for each cell line, in addition to confirming that each cell line is derived from a different clonal isolate. We will use linear amplification mediated PCR (LAM-PCR) to recover and sequence the site(s) of transgene integration in each clone. Finally, the chromosomal site(s) of transgene insertion in each clone will be determined by fluorescent in situ hybridization (FISH) using vector-specific probes. We will eliminate clones from further consideration if Southern blot analysis indicates that transgene arrays have integrated at multiple genomic sites or if insertion site heterogeneity exists within any given clone.

Karyotype Analysis.

Cytogenetic analysis of the NIKS$^{IL-12}$ candidate clones will be performed to identify and eliminate any rare clones that may have acquired karyotypic changes during clonal selection. Sub-confluent cultures of each clone will be analyzed by G-banded karyotype analysis. Any clonal cell line that displays cytogenetic changes from the parental NIKS® cell line will be eliminated from further development.

Anchorage-Independent Growth Assay.

Anchorage-independent growth is highly correlated with tumorigenicity in vivo. For this reason, the anchorage-independent growth characteristics of NIKS$^{IL-12}$ cells will be assayed in agar or methylcellulosecontaining medium as recommended in the FDA document "Points to Consider in the Characterization of Cell Lines Used to Produce Biologicals (1993)". Preconfluent cultures of each of the three candidate clones will be suspended at $6 \times 10^3$ cells per ml in serum-supplemented growth medium containing 0.3% agar or 1.68% methylcellulose. Cells will be photographed in situ in the agar or methylcellulose-containing medium. After 4 weeks non-tumorigenic NIKS$^{IL-12}$ cells should remain as single cells. The assays will be continued for a total of 8 weeks, in order to ensure that no slow growing variants of the NIKS$^{IL-12}$ cells arise. Untransfected NIKS® cells and SCC4 cells will be included as negative and positive controls. Any clonal cell line that displays anchorage-independent growth will not be advanced to the animal model study.

Example 7: Assessment of the Ability of NIKS$^{IL-12}$ Cells to Suppress the Growth of Human Tumor Xenografts in Hu-PBL-NOD-SCID IL2Rγ$^{null}$ Mice Two animal models are proposed to determine whether NIKS® cells secreting elevated levels of IL-12 are able to stimulate the anti-tumor activity of human PBLs. The first will utilize a co-injection strategy of human tumor cells and PBLs mixed with IL-12 expressing NIKS® cells to evaluate the bioactivity of NIKS$^{IL-12}$ clones. The second model simulates the anticipated clinical application of this approach, where NIKS$^{IL-12}$ cells are administered topically in the context of stratified skin substitute tissue to suppress the growth of underlying tumor cells.

Evaluation of Co-Injected NIKS$^{IL-12}$ Cells with Tumors and Hu-PBL.

Because human IL-12 does not elicit biological responses in mouse lymphocytes, it is not possible to evaluate the anti-tumor activity of human IL-12 against murine tumors. To evaluate the ability of tissue secreting elevated levels of IL-12 to suppress the growth of human tumors, we will utilize a modification of the SCID-Winn model [15], in which mixed xenografts of human tumor cells and human PBLs are established in immunodeficient mice. This model has been used to demonstrate that local or systemic human IL-12 is able to stimulate the anti-tumor activity of the engrafted human PBLs (Iwanuma et al., Cancer Res, 57(14): 2937-42 (1997) and Egilmez et al., J Immunother, 23(2): 190-5 (2000)). It has also been demonstrated that a tripartite injection strategy using human tumor cells, human PBLs, and biodegradable IL-12 microspheres results in IL-12 dependent suppression of tumor growth (Egilmez et al., J Immunother, 23(2): 190-5 (2000)). Because SCID mice have normal NK function and often exhibit a "leaky" T and B cell phenotype, the NOD-scid IL2Rγ$^{null}$ mouse strain will be used for these studies. These mice are homozygous for the Prkdc$^{scid}$ mutation and are also homozygous for a knockout of IL2Rg, which encodes the cytokine receptor common gamma chain; a component of the IL-2 receptor complex and several other lymphoid cytokine receptors. The double mutant mice lack mature T and B lymphocytes, have greatly reduced NK activity, and do not develop spontaneous lymphomas which are problematic in SCID and NOD-scid mice [14, 61]. NOD-scid IL2Rγ$^{null}$ mice have been used to evaluate the anti-tumor activity of IL-12 against human tumor xenografts (Simpson-Abelson et al., J Immunol, 180 (10): 7009-18 (2008)). NOD-scid IL2Rγ$^{null}$ mice will be purchased from The Jackson Laboratory (Bar Harbor, Me.). Because human PBL from different donors exhibit different degrees of baseline reactivity against allogeneic tumor cells (Iwanuma et al., Cancer Res, 57(14): 2937-42, 1997)), initial titration studies will be performed to determine a ratio of PBL to tumor cells that exhibits IL-12-dependent stimulation of HuPBL anti-tumor activity. Human PBLs will be obtained from a healthy consented adult donor by leukapheresis followed by lysis of RBCs with 0.83% NH4Cl. PBLs will be washed twice in Hank's balanced salt solution containing 0.5% BSA. For these studies, we will utilize the human SCC4 cell line, which was derived from a squamous cell carcinoma of the tongue (Rheinwald and Beckett, Cancer Res, 41(5): 1657-63, 1981)). This cell line reliably generates rapidly growing tumors when implanted subcutaneously in immunodeficient mice. However, if the SCC4 line fails to generate tumors when co-injected with HuPBL, we will evaluate other SCC lines. If tumor formation with SCC cells proves problematic, we will consider using one of the eight melanoma cell lines that are among 60 tumor cell lines used by the NCI's Developmental Therapeutics Program. Ten mice will each be injected subcutaneously with a mixture of $1 \times 10^6$ tumor cells and $1 \times 10^6$ NIKS® cells either alone or in combination with $5 \times 10^6$, $1 \times 10^7$, or $2 \times 10^7$ human PBLs (Table 1). Five mice from each PBL:tumor ratio will receive rhIL-12 (1 µg/mouse) by IP injection every other day for 3 weeks. The growth of implanted tumor cells will be monitored weekly for six weeks by measuring the length and width and determining the tumor volume using the formula v=l×w2/2. The ratio of HuPBL to tumor cells that exhibits the most significant enhancement of tumor suppression by IL-12 between three and six weeks after injection will be used for subsequent studies. PBL from the same donor will be co-injected with tumor cells at this ratio for experiments examining inhibition of tumor growth by NIKS$^{IL-12}$ cells.

TABLE 1

Titration of HuPBL for Mixed Human Tumor Xenografts

| Group (n = 5) | Xenograft mixture/IL-12 |
|---|---|
| 1 | Tumor + NIKS ® |
| 2 | Tumor + NIKS ® + IL-12 |
| 3 | Tumor + NIKS ® + 5 × 10$^6$ HuPBL |
| 4 | Tumor + NIKS ® + 5 × 10$^6$ HuPBL + IL-12 |
| 5 | Tumor + NIKS ® + 1 × 10$^7$ HuPBL |
| 6 | Tumor + NIKS ® + 1 × 10$^7$ HuPBL + IL-12 |
| 7 | Tumor + NIKS ® + 5 × 10$^7$ HuPBL |
| 8 | Tumor + NIKS ® + 2 × 10$^7$ HuPBL + IL-12 |

To assess the ability of NIKS$^{IL-12}$ cells to stimulate the anti-tumor activity of HuPBLs, we will inject mixtures of 1×10$^6$ tumor cells and either 1×10$^6$ unmodified NIKS® cells or 1×10$^6$ NIKS$^{IL-12}$ cells, in the presence or absence of HuPBL at the optimal ratio defined above (see Table 2).

TABLE 2

Experimental Xenograft Groups

| Group (n = 5) | Xenograft mixture/IL-12 |
|---|---|
| 1 | Tumor only |
| 2 | NIKS ® + Tumor |
| 3 | NIKS ® + Tumor + HuPBL |
| 4 | NIKS ® + Tumor + HuPBL + IL-12 |
| 5 | NIKS$^{IL-12}$ (high) + Tumore |
| 6 | NIKS$^{IL-12}$ (high) + Tumor + HuPBL |
| 7 | NIKS$^{IL-12}$ (med) + Tumor |
| 8 | NIKS$^{IL-12}$ (med) + Tumor + HuPBL |
| 9 | NIKS$^{IL-12}$ (low) + Tumor |
| 10 | NIKS$^{IL-12}$ (low) + Tumor + HuPBL |

Animals will be monitored for eight weeks after xenograft implantation. Circulating levels of human IL-12 and IFN-γ in serum will be determined weekly by ELISA. The growth of implanted tumor cells will be monitored weekly by measuring the length and width and determining the tumor volume using the formula v=1×w2/2. In addition, the percentage of mice in each group that are free of detectable tumors will be determined weekly. Statistical analysis of tumor growth between groups will be performed using an unpaired Student's t-test, with significant differences being assigned if the p-value is <0.05. At the time of sacrifice, histological sections will be prepared from the tumors or injection sites of all animals. These sections will be stained with H&E to determine the overall level of lymphocytic infiltrate in the tumors. Clones that result in statistically-significant decreases in tumor growth or the percentage of tumor-containing mice for at least three consecutive weeks will be carried forward.

Example 8: Stimulation of Anti-Tumor Activity by NIKS$^{IL-12}$ Skin Substitute Tissue This experiment is designed to mimic the ultimate clinical use of bioengineered skin tissue to prevent the growth or spread of residual tumor cells that may remain in wounds following tumor resection by Moh's surgery. For these studies, mice will first be grafted with skin substitute tissue prepared from NIKS$^{IL-12}$ clones expressing high, medium, or low levels of IL-12 using procedures that we routinely use to engraft human skin substitute tissue. Tissue is produced in a circular shape with a surface area of 44 cm2 and will be trimmed to fit the wounds immediately prior to engraftment Skin substitute tissue expressing elevated levels of IL-12 will be prepared by seeding dermal equivalents with NIKS$^{IL-12}$ cells and culturing for 14 days. Prior to grafting, secreted IL-12 levels will be assessed in conditioned media harvested from StrataGraft® and NIKS$^{IL-12}$ tissues. Full-thickness excisional wounds (1.5×2 cm) will be created on the backs of forty-five anesthetized NODscid IL2Rγ$^{null}$ mice. The wounds of three groups of ten mice will be covered with tissue prepared with NIKS$^{IL-12}$ tissue secreting high, medium, or low levels of IL-12 (ExpressGraft$^{IL12}$). A fourth group of fifteen mice will be grafted with tissue prepared from unmodified NIKS® cells. Treated wounds will be covered with non-adherent gauze bandages saturated with antibiotic ointment and occlusive bandages to maintain a moist environment. One week after placement of tissue, bandages will be removed. Mixtures of 1×10$^6$ human tumor cells and freshly-isolated HuPBL in the optimal ratio determined above will be injected subcutaneously underneath the engrafted human skin substitute tissue in five animals grafted with each tissue type (Table 3). Another group of five mice will receive injections of 1×10$^6$ tumor cells only. A final group of five control animals that were grafted with unmodified NIKS® tissue will be injected with a mixture of tumor cells and HuPBL and will also receive IP injections of rhIL-12 (1 µg/mouse) every other day for 3 weeks. Animals will be monitored for eight weeks after xenograft implantation.

Circulating levels of human IL-12 and IFN-γ in serum will be determined weekly by ELISA. The growth of implanted tumor cells will be monitored weekly by measuring the length and width and determining the tumor volume using the formula v=1×w2/2. The percentage of mice in each group that are free of detectable tumors will be determined weekly. Statistical analysis of tumor growth between groups will be performed using an unpaired Student's t-test, with significant differences being assigned if the p-value is <0.05. At the time of sacrifice, histological sections will be prepared from the tumors or injection sites of all animals. These sections will be stained with H&E to determine the overall level of lymphocytic infiltrate in the tumors.

TABLE 3

Experimental Xenograft Groups

| Group (n = 5) | Skin tissue type | Tumor Xenograft |
|---|---|---|
| 1 | NIKS ® | Tumor only |
| 2 | NIKS ® | Tumor + HuPBL |
| 3 | NIKS ® | Tumor + HuPBL + IL-12 |
| 4 | NIKS$^{IL-12}$ (high) | Tumor only |
| 5 | NIKS$^{IL-12}$ (high) | Tumor + HuPBL |
| 6 | NIKS$^{IL-12}$ (med) | Tumor + HuPBL + IL-12 |
| 7 | NIKS$^{IL-12}$ (med) | Tumor only |
| 8 | NIKS$^{IL-12}$ (low) | Tumor + HuPBL |
| 9 | NIKS$^{IL-12}$ (low) | Tumor + HuPBL + IL-12 |

REFERENCES

1. Leonard, J. P., et al., *Effects of single-dose interleukin-12 exposure on interleukin-12-associated toxicity and interferon-gamma production*. Blood, 1997. 90(7): p. 2541-8.
2. Ansell, S. M., et al., *Randomized phase II study of interleukin-12 in combination with rituximab in previ-* ously treated non-Hodgkin's lymphoma patients. Clin Cancer Res, 2006. 12(20 Pt 1): p. 6056-63.
3. Lenzi, R., et al., *Phase II study of intraperitoneal recombinant interleukin-12 (rhIL-12) in patients with peritoneal carcinomatosis (residual disease <1 cm) associated with ovarian cancer or primary peritoneal carcinoma*. J Transl Med, 2007. 5: p. 66.
4. Lenzi, R., et al., *Phase I study of intraperitoneal recombinant human interleukin 12 in patients with Mullerian carcinoma, gastrointestinal primary malignancies, and mesothelioma*. Clin Cancer Res, 2002. 8(12): p. 3686-95.
5. Heinzerling, L., et al., *Intratumoral injection of DNA encoding human interleukin 12 into patients with metastatic melanoma: clinical efficacy*. Hum Gene Ther, 2005. 16(1): p. 35-48.
6. Mahvi, D. M., et al., *Intratumoral injection of IL-12 plasmid DNA—results of a phase I/IB clinical trial*. Cancer Gene Ther, 2007. 14(8): p. 717-23.
7. Allen-Hoffmann, B. L., et al., *Normal Growth and Differentiation in a Spontaneously Immortalized Near-Diploid Human Keratinocyte Cell Line, NIKS*. Journal of Investigative Dermatology, 2000. 114(3): p. 444-455.
8. Parish, C. R., *Cancer immunotherapy: the past, the present and the future*. Immunol Cell Biol, 2003. 81(2): p. 106-13.
9. Burnet, F. M., *Immunological aspects of malignant disease*. Lancet, 1967. 1(7501): p. 1171-4.
10. Lanier, L. L., *A renaissance for the tumor immunosurveillance hypothesis*. Nat Med, 2001. 7(11): p. 1178-80.
11. Wang, E., et al., *Spontaneous and treatment-induced cancer rejection in humans*. Expert Opin Biol Ther, 2008. 8(3): p. 337-49.
12. Colombo, M. P. and G. Trinchieri, *Interleukin-12 in anti-tumor immunity and immunotherapy*. Cytokine Growth Factor Rev, 2002. 13(2): p. 155-68.
13. Weiss, J. M., et al., *Immunotherapy of cancer by IL-12-based cytokine combinations*. Expert Opin Biol Ther, 2007. 7(11): p. 1705-21.
14. Simpson-Abelson, M. R., et al., *Long-term engraftment and expansion of tumor-derived memory T cells following the implantation of non-disrupted pieces of human lung tumor into NOD-scid IL2Rgamma(null) mice*. J Immunol, 2008. 180(10): p. 7009-18.
15. Iwanuma, Y., et al., *Antitumor immune response of human peripheral blood lymphocytes coengrafted with tumor into severe combined immunodeficient mice*. Cancer Res, 1997. 57(14): p. 2937-42.
16. Langrish, C. L., et al., *IL-12 and IL-23: master regulators of innate and adaptive immunity*. Immunol Rev, 2004. 202: p. 96-105.
17. Broderick, L., et al., *Human CD4+ effector memory T cells persisting in the microenvironment of lung cancer xenografts are activated by local delivery of IL-12 to proliferate, produce IFN-gamma, and eradicate tumor cells*. J Immunol, 2005. 174(2): p. 898-906.
18. Hess, S. D., et al., *Human CD4+ T cells present within the microenvironment of human lung tumors are mobilized by the local and sustained release of IL-12 to kill tumors in situ by indirect effects of IFNgamma*. J Immunol, 2003. 170(1): p. 400-12.
19. Kilinc, M. O., et al., *Reversing tumor immune suppression with intratumoral IL-12: activation of tumorassociated T effector/memory cells, induction of T suppressor apoptosis, and infiltration of CD8+T effectors*. J Immunol, 2006. 177(10): p. 6962-73.
20. Park, A. Y., et al., *The role of IL-12 in maintaining resistance to Leishmania major*. J Immunol, 2002. 168 (11): p. 5771-7.
21. Oppmann, B., et al., *Novel p19 protein engages IL-12p40 to form a cytokine, IL-23, with biological activities similar as well as distinct from IL-12*. Immunity, 2000. 13(5): p. 715-25.
22. Gillessen, S., et al., *Mouse interleukin-12 (IL-12) p40 homodimer: a potent IL-12 antagonist*. Eur J Immunol, 1995. 25(1): p. 200-6.
23. Ling, P., et al., *Human IL-12 p40 homodimer binds to the IL-12 receptor but does not mediate biologic activity*. J Immunol, 1995. 154(1): p. 116-27.
24. Mattner, F., et al., *The interleukin-12 subunit p40 specifically inhibits effects of the interleukin-12 heterodimer*. Eur J Immunol, 1993. 23(9): p. 2202-8.
25. Lieschke, G. J., et al., *Bioactive murine and human interleukin-12 fusion proteins which retain antitumor activity in vivo*. Nat Biotechnol, 1997. 15(1): p. 35-40.
26. Foss, D. L., et al., *In vitro and in vivo bioactivity of single-chain interleukin-12*. Scand J Immunol, 1999. 50(6): p. 596-604.
27. Anderson, R., et al., *Construction and biological characterization of an interleukin-12 fusion protein (Flexi-12): delivery to acute myeloid leukemic blasts using adeno-associated virus*. Hum Gene Ther, 1997. 8(9): p. 1125-35.
28. Presky, D. H., et al., *A functional interleukin 12 receptor complex is composed of two beta-type cytokine receptor subunits*. Proc Natl Acad Sci USA, 1996. 93(24): p. 14002-7.
29. Becskei, A. and M. J. Grusby, *Contribution of IL-12R mediated feedback loop to Th1 cell differentiation*. FEBS Lett, 2007. 581(27): p. 5199-206.
30. Rogge, L., et al., *Selective expression of an interleukin-12 receptor component by human T helper 1 cells*. J Exp Med, 1997. 185(5): p. 825-31.
31. Ma, X., et al., *The interleukin 12 p40 gene promoter is primed by interferon gamma in monocytic cells*. J Exp Med, 1996. 183(1): p. 147-57.
32. Kanegane, C., et al., *Contribution of the CXC chemokines IP-10 and Mig to the antitumor effects of IL-12*. J Leukoc Biol, 1998. 64(3): p. 384-92.
33. Grufman, P. and K. Karre, *Innate and adaptive immunity to tumors: IL-12 is required for optimal responses*. Eur J Immunol, 2000. 30(4): p. 1088-93.
34. Wigginton, J. M. and R. H. Wiltrout, *IL-12/IL-2 combination cytokine therapy for solid tumours: translation from bench to bedside*. Expert Opin Biol Ther, 2002. 2(5): p. 513-24.
35. Chen, X., et al., *A tumor-selective biotherapy with prolonged impact on established metastases based on cytokine gene-engineered MSCs*. Mol Ther, 2008. 16(4): p. 749-56.
36. Dempsey, M. P., et al., *Using genetically modified microvascular free flaps to deliver local cancer immunotherapy with minimal systemic toxicity*. Plast Reconstr Surg, 2008. 121(5): p. 1541-53.
37. Eliopoulos, N., et al., *Neo-organoid of marrow mesenchymal stromal cells secreting interleukin-12 for breast cancer therapy*. Cancer Res, 2008. 68(12): p. 4810-8.
38. Egilmez, N. K., et al., *Cytokines delivered by biodegradable microspheres promote effective suppression of human tumors by human peripheral blood lymphocytes in the SCID-Winn model*. J Immunother, 2000. 23(2): p. 190-5.

39. Schoenhaut, D. S., et al., *Cloning and expression of murine IL-12.* J Immunol, 1992. 148(11): p. 3433-40.
40. Curran, M. P. and G. L. Plosker, *Bilayered bioengineered skin substitute (Apligraf): a review of its use in the treatment of venous leg ulcers and diabetic foot ulcers.* BioDrugs, 2002. 16(6): p. 439-55.
41. Eaglstein, W. H., M. Iriondo, and K. Laszlo, *A composite skin substitute (graftskin) for surgical wounds. A clinical experience.* Dermatol Surg, 1995. 21(10): p. 839-43.
42. Trent, J. F. and R. S. Kirsner, *Tissue engineered skin: Apligraf, a bi-layered living skin equivalent.* International Journal of Clinical Practice, 1998. 52(6): p. 408-413.
43. Wilkins, L. M., et al., *Development of a Bilayered Living Skin Construct For Clinical Applications.* Biotechnology and Bioengineering, 1994. 43(8): p. 747-756.
44. Nemecek, G. M. and A. D. Dayan, *Safety evaluation of human living skin equivalents.* Toxicol Pathol, 1999. 27(1): p. 101-3.
45. Gielen, V., et al., *Progressive replacement of human cultured epithelial allografts by recipient cells as evidenced by HLA class I antigens expression.* Dermatologica, 1987. 175(4): p. 166-70.
46. Griffiths, M., et al., *Survival of Apligraf in acute human wounds.* Tissue Eng, 2004. 10(7-8): p. 1180-95.
47. Becker, G. D., L. A. Adams, and B. C. Levin, *Mohs wounds of the forehead: healing by secondary intention.* J Wound Care, 1998. 7(10): p. 497-500.
48. Falanga, V. and M. Sabolinski, *A bilayered living skin construct (APLIGRAF) accelerates complete closure of hard-to-heal venous ulcers.* Wound Repair Regen, 1999. 7(4): p. 201-7.
49. Veves, A., et al., *Graftskin, a human skin equivalent, is effective in the management of noninfected neuropathic diabetic foot ulcers: a prospective randomized multicenter clinical trial.* Diabetes Care, 2001. 24(2): p. 290-5.
50. Gohari, S., et al., *Evaluation of tissue-engineered skin (human skin substitute) and secondary intention healing in the treatment of full thickness wounds after Mohs micrographic or excisional surgery.* Dermatol Surg, 2002. 28(12): p. 1107-14; discussion 1114.
51. Tarlow, M. M., R. Nossa, and J. M. Spencer, *Effective management of difficult surgical defects using tissue-engineered skin.* Dermatol Surg, 2001. 27(1): p. 71-4.
52. Muller, G., et al., *Identification and induction of human keratinocyte-derived IL-12.* J Clin Invest, 1994. 94(5): p. 1799-805.
53. Yawalkar, N., et al., *Constitutive expression of both subunits of interleukin-12 in human keratinocytes.* J Invest Dermatol, 1996. 106(1): p. 80-3.
54. Aragane, Y., et al., *IL-12 is expressed and released by human keratinocytes and epidermoid carcinoma cell lines.* J Immunol, 1994. 153(12): p. 5366-72.
55. Glover, D. J., H. J. Lipps, and D. A. Jans, *Towards safe, non-viral therapeutic gene expression in humans.* Nat Rev Genet, 2005. 6(4): p. 299-310.
56. *Guidance for Human Somatic Cell Therapy and Gene Therapy*, U.F.a.D. Administration, Editor. 1998.
57. NIH, *NIH Guidelines for Research Involving Recombinant DNA Molecules.* 2002.
58. Gately, M. K., R. Chizzonite, and D. H. Presky, *Measurement of human and mouse interleukin-12.* Curr Protoc Immunol, 2001. Chapter 6: p. Unit 6 16.
59. FDA, *Guidance for FDA Review Staff and Sponsors: Content and Review of Chemistry, Manufacturing, and Control (CMC) Information for Human Gene Therapy Investigational New Drug Applications (INDs),* F.D.A. Department of Health and Human Services, Center for Biologics Evaluation and Research, Editor. 2004.
60. Shin, S. I., et al., *Tumorigenicity of virus-transformed cells in nude mice is correlated specifically with anchorage independent growth in vitro.* Proc Natl Acad Sci USA, 1975. 72(11): p. 4435-9.
61. Shultz, L. D., et al., *Human lymphoid and myeloid cell development in NOD/LtSz-scid IL2R gamma null mice engrafted with mobilized human hemopoietic stem cells.* J Immunol, 2005. 174(10): p. 6477-89.
62. Rheinwald, J. G. and M. A. Beckett, *Tumorigenic keratinocyte lines requiring anchorage and fibroblast support cultures from human squamous cell carcinomas.* Cancer Res, 1981. 41(5): p. 1657-63.
63. *Points to Consider in the Characterization of Cell Lines Used to Produce Biologicals,* F.D.A. Department of Health and Human Services, Center for Biologics Evaluation and Research, Editor. 1993.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology, biochemistry, or related fields are intended to be within the scope of the following claims.

What is claimed is:

1. A method of treating a wound bed resulting from removal of a skin cancer in a patient, comprising:
   a) providing a human skin substitute comprising cells expressing exogenous Interleukin-12, wherein the cells are selected from the group consisting of primary keratinocytes, keratinocyte precursors, transdifferentiated keratinocytes, and immortalized keratinocytes, wherein said skin substitute comprises a stratified squamous epithelium comprising said cells expressing exogenous Interleukin-12 supported on a dermal equivalent; and
   b) placing said human skin substitute on said wound bed resulting from removal of a skin cancer in said patient such that the dermal equivalent is in contact with the wound bed and separates the wound bed from the cells expressing exogenous Interleukin-12.

2. The method of claim 1, wherein said skin cancer is selected from the group consisting of melanoma and basal cell carcinoma.

3. The method of claim 1, wherein said human skin substitute inhibits the spread of said skin cancer.

4. The method of claim 1, wherein said human skin substitute produces amounts of bioactive IL-12 sufficient for inducing the proliferation of PHA-stimulated lymphoblasts.

5. The method of claim 1, wherein said exogenous IL-12 is a fusion of the p35 and p40 IL-12 subunits.

6. The method of claim 5, wherein said fusion protein has the amino acid sequence of SEQ ID NO:3.

7. The method of claim 6, wherein said human skin substitute comprises near diploid immortalized keratinocytes (NIKS) cells.

8. A method of treating a wound bed resulting from removal of a skin cancer in a patient, comprising:
  a) providing a human skin substitute comprising cells expressing exogenous Interleukin-12, wherein the cells are selected from the group consisting of primary keratinocytes, keratinocyte precursors, transdifferentiated keratinocytes, and immortalized keratinocytes, wherein said skin substitute comprises a stratified squamous epithelium comprising said cells expressing exogenous Interleukin-12 supported on a dermal equivalent; and
  b) placing said human skin substitute on said wound bed resulting from removal of a skin cancer in said patient such that the dermal equivalent is in direct contact with the wound bed and separates the wound bed from the cells expressing exogenous Interleukin-12;
  wherein the human skin substitute suppresses growth of cancer cells in the wound bed.

9. A method of treating a wound bed resulting from removal of a skin cancer in a patient, comprising:
  a) providing a human skin substitute comprising cells expressing exogenous Interleukin-12, wherein the cells are selected from the group consisting of primary keratinocytes, keratinocyte precursors, transdifferentiated keratinocytes, and immortalized keratinocytes, wherein said skin substitute comprises a stratified squamous epithelium comprising said cells expressing exogenous Interleukin-12 supported on a dermal equivalent; and
  b) placing said human skin substitute on said wound bed resulting from 9 removal of a skin cancer in said patient such that the dermal equivalent is in direct contact with the wound bed and separates the wound bed from the cells expressing exogenous Interleukin-12;
  wherein the human skin substitute stimulates an immune response against residual cancer cells in the wound bed.

* * * * *

SEQUENCE LISTING

```
<160> NUMBER OF SEQ ID NOS: 6

<210> SEQ ID NO 1
<211> LENGTH: 253
<212> TYPE: PRT
<213> ORGANISM: Homo sapiens

<400> SEQUENCE: 1

Met Trp Pro Pro Gly Ser Ala Ser Gln Pro Pro Pro Ser Pro Ala Ala
1               5                   10                  15

Ala Thr Gly Leu His Pro Ala Ala Arg Pro Val Ser Leu Gln Cys Arg
            20                  25                  30

Leu Ser Met Cys Pro Ala Arg Ser Leu Leu Leu Val Ala Thr Leu Val
```

```
                35                  40                  45
Leu Leu Asp His Leu Ser Leu Ala Arg Asn Leu Pro Val Ala Thr Pro
 50                  55                  60

Asp Pro Gly Met Phe Pro Cys Leu His His Ser Gln Asn Leu Leu Arg
 65                  70                  75                  80

Ala Val Ser Asn Met Leu Gln Lys Ala Arg Gln Thr Leu Glu Phe Tyr
                     85                  90                  95

Pro Cys Thr Ser Glu Glu Ile Asp His Glu Asp Ile Thr Lys Asp Lys
                100                 105                 110

Thr Ser Thr Val Glu Ala Cys Leu Pro Leu Glu Leu Thr Lys Asn Glu
                115                 120                 125

Ser Cys Leu Asn Ser Arg Glu Thr Ser Phe Ile Thr Asn Gly Ser Cys
130                 135                 140

Leu Ala Ser Arg Lys Thr Ser Phe Met Met Ala Leu Cys Leu Ser Ser
145                 150                 155                 160

Ile Tyr Glu Asp Leu Lys Met Tyr Gln Val Glu Phe Lys Thr Met Asn
                165                 170                 175

Ala Lys Leu Leu Met Asp Pro Lys Arg Gln Ile Phe Leu Asp Gln Asn
                180                 185                 190

Met Leu Ala Val Ile Asp Glu Leu Met Gln Ala Leu Asn Phe Asn Ser
                195                 200                 205

Glu Thr Val Pro Gln Lys Ser Ser Leu Glu Glu Pro Asp Phe Tyr Lys
210                 215                 220

Thr Lys Ile Lys Leu Cys Ile Leu Leu His Ala Phe Arg Ile Arg Ala
225                 230                 235                 240

Val Thr Ile Asp Arg Val Met Ser Tyr Leu Asn Ala Ser
                245                 250

<210> SEQ ID NO 2
<211> LENGTH: 328
<212> TYPE: PRT
<213> ORGANISM: Homo sapiens

<400> SEQUENCE: 2

Met Cys His Gln Gln Leu Val Ile Ser Trp Phe Ser Leu Val Phe Leu
 1               5                  10                  15

Ala Ser Pro Leu Val Ala Ile Trp Glu Leu Lys Lys Asp Val Tyr Val
                 20                  25                  30

Val Glu Leu Asp Trp Tyr Pro Asp Ala Pro Gly Glu Met Val Val Leu
                 35                  40                  45

Thr Cys Asp Thr Pro Glu Glu Asp Gly Ile Thr Trp Thr Leu Asp Gln
 50                  55                  60

Ser Ser Glu Val Leu Gly Ser Gly Lys Thr Leu Thr Ile Gln Val Lys
 65                  70                  75                  80

Glu Phe Gly Asp Ala Gly Gln Tyr Thr Cys His Lys Gly Gly Glu Val
                 85                  90                  95

Leu Ser His Ser Leu Leu Leu Leu His Lys Lys Glu Asp Gly Ile Trp
                100                 105                 110

Ser Thr Asp Ile Leu Lys Asp Gln Lys Glu Pro Lys Asn Lys Thr Phe
                115                 120                 125

Leu Arg Cys Glu Ala Lys Asn Tyr Ser Gly Arg Phe Thr Cys Trp Trp
                130                 135                 140

Leu Thr Thr Ile Ser Thr Asp Leu Thr Phe Ser Val Lys Ser Ser Arg
145                 150                 155                 160
```

```
Gly Ser Ser Asp Pro Gln Gly Val Thr Cys Gly Ala Ala Thr Leu Ser
            165                 170                 175

Ala Glu Arg Val Arg Gly Asp Asn Lys Glu Tyr Glu Tyr Ser Val Glu
        180                 185                 190

Cys Gln Glu Asp Ser Ala Cys Pro Ala Ala Glu Glu Ser Leu Pro Ile
    195                 200                 205

Glu Val Met Val Asp Ala Val His Lys Leu Lys Tyr Glu Asn Tyr Thr
210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
            245                 250                 255

Glu Tyr Pro Asp Thr Trp Ser Thr Pro His Ser Tyr Phe Ser Leu Thr
        260                 265                 270

Phe Cys Val Gln Val Gln Gly Lys Ser Lys Arg Glu Lys Lys Asp Arg
    275                 280                 285

Val Phe Thr Asp Lys Thr Ser Ala Thr Val Ile Cys Arg Lys Asn Ala
290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
            325

<210> SEQ ID NO 3
<211> LENGTH: 566
<212> TYPE: PRT
<213> ORGANISM: Artificial Sequence
<220> FEATURE:
<223> OTHER INFORMATION: Synthetic

<400> SEQUENCE: 3

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190
```

```
Cys Gln Glu Asp Ser Ala Cys Pro Ala Ala Glu Glu Ser Leu Pro Ile
            195                 200                 205
Glu Val Met Val Asp Ala Val His Lys Leu Lys Tyr Glu Asn Tyr Thr
210                 215                 220
Ser Ser Phe Phe Ile Arg Asp Ile Ile Lys Pro Asp Pro Lys Asn
225                 230                 235                 240
Leu Gln Leu Lys Pro Leu Lys Asn Ser Arg Gln Val Glu Val Ser Trp
                245                 250                 255
Glu Tyr Pro Asp Thr Trp Ser Thr Pro His Ser Tyr Phe Ser Leu Thr
                260                 265                 270
Phe Cys Val Gln Val Gln Gly Lys Ser Lys Arg Glu Lys Lys Asp Arg
            275                 280                 285
Val Phe Thr Asp Lys Thr Ser Ala Thr Val Ile Cys Arg Lys Asn Ala
290                 295                 300
Ser Ile Ser Val Arg Ala Gln Asp Arg Tyr Tyr Ser Ser Ser Trp Ser
305                 310                 315                 320
Glu Trp Ala Ser Val Pro Cys Ser Gly Gly Gly Gly Ser Ala
                325                 330                 335
Ala Arg Pro Val Ser Leu Gln Cys Arg Leu Ser Met Cys Pro Ala Arg
                340                 345                 350
Ser Leu Leu Leu Val Ala Thr Leu Val Leu Leu Asp His Leu Ser Leu
            355                 360                 365
Ala Arg Asn Leu Pro Val Ala Thr Pro Asp Pro Gly Met Phe Pro Cys
            370                 375                 380
Leu His His Ser Gln Asn Leu Leu Arg Ala Val Ser Asn Met Leu Gln
385                 390                 395                 400
Lys Ala Arg Gln Thr Leu Glu Phe Tyr Pro Cys Thr Ser Glu Glu Ile
                405                 410                 415
Asp His Glu Asp Ile Thr Lys Asp Lys Thr Ser Thr Val Glu Ala Cys
                420                 425                 430
Leu Pro Leu Glu Leu Thr Lys Asn Glu Ser Cys Leu Asn Ser Arg Glu
            435                 440                 445
Thr Ser Phe Ile Thr Asn Gly Ser Cys Leu Ala Ser Arg Lys Thr Ser
450                 455                 460
Phe Met Met Ala Leu Cys Leu Ser Ser Ile Tyr Glu Asp Leu Lys Met
465                 470                 475                 480
Tyr Gln Val Glu Phe Lys Thr Met Asn Ala Lys Leu Leu Met Asp Pro
                485                 490                 495
Lys Arg Gln Ile Phe Leu Asp Gln Asn Met Leu Ala Val Ile Asp Glu
                500                 505                 510
Leu Met Gln Ala Leu Asn Phe Asn Ser Glu Thr Val Pro Gln Lys Ser
            515                 520                 525
Ser Leu Glu Glu Pro Asp Phe Tyr Lys Thr Lys Ile Lys Leu Cys Ile
530                 535                 540
Leu Leu His Ala Phe Arg Ile Arg Ala Val Thr Ile Asp Arg Val Met
545                 550                 555                 560
Ser Tyr Leu Asn Ala Ser
                565

<210> SEQ ID NO 4
<211> LENGTH: 1021
<212> TYPE: DNA
<213> ORGANISM: Homo sapiens

<400> SEQUENCE: 4
```

-continued

```
cgggagttaa tccgaaagcg ccgcaagccc cgcgggccgg ccgcaccgca cgtgtcaccg      60
agaagctgat gtagagagag acacagaagg agacagaaag caagagacca gagtcccggg     120
aaagtcctgc cgcgcctcgg gacaattata aaaatgtggc ccctgggtc agcctcccag      180
ccaccgccct cacctgccgc ggccacaggt ctgcatccag cggctcgccc tgtgtccctg     240
cagtgccggc tcagcatgtg tccagcgcgc agcctcctcc ttgtggctac cctggtcctc     300
ctggaccacc tcagtttggc cagaaacctc cccgtggcca ctccagaccc aggaatgttc     360
ccatgccttc accactccca aaacctgctg agggccgtca gcaacatgct ccagaaggcc     420
agacaaactc tagaatttta cccttgcact tctgaagaga ttgatcatga agatatcaca     480
aaagataaaa ccagcacagt ggaggcctgt ttaccattgg aattaaccaa gaatgagagt     540
tgcctaaatt ccagagagac ctcttttcata actaatggga gttgcctggc ctccagaaag     600
acctctttta tgatggccct gtgccttagt agtatttatg aagacttgaa gatgtaccag     660
gtggagttca agaccatgaa tgcaaagctt ctgatggatc ctaagaggca gatctttcta     720
gatcaaaaca tgctggcagt tattgatgag ctgatgcagg ccctgaattt caacagtgag     780
actgtgccac aaaaatcctc ccttgaagaa ccggattttt ataaaactaa aatcaagctc     840
tgcatacttc ttcatgcttt cagaattcgg gcagtgacta ttgatagagt gatgagctat     900
ctgaatgctt cctaaaaagc gaggtccctc caaaccgttg tcatttttat aaaactttga     960
aatgaggaaa ctttgatagg atgtggatta agaactaggg agggggaaag aaggatggga    1020
c                                                                    1021
```

<210> SEQ ID NO 5
<211> LENGTH: 1046
<212> TYPE: DNA
<213> ORGANISM: Homo sapiens

<400> SEQUENCE: 5

```
ccattggact ctccgtcctg cccagagcaa gatgtgtcac cagcagttgg tcatctcttg      60
gttttccctg gttttctgg catctcccct cgtggccata tgggaactga agaaagatgt     120
ttatgtcgta gaattggatt ggtatccgga tgccctgga gaaatggtgg tcctcacctg     180
tgacacccct gaagaagatg gtatcacctg gaccttggac cagagcagtg aggtcttagg     240
ctctggcaaa accctgacca tccaagtcaa agagtttgga gatgctggcc agtacacctg     300
tcacaaagga ggcgaggttc taagccattc gctcctgctg cttcacaaaa aggaagatgg     360
aatttggtcc actgatattt taaaggacca gaaagaaccc aaaaataaga cctttctaag     420
atgcgaggcc aagaattatt ctggacgttt cacctgctgg tggctgacga caatcagtac     480
tgatttgaca ttcagtgtca aaagcagcag aggctcttct gacccccaag gggtgacgtg     540
cggagctgct acactctctg cagagagagt cagaggggac aacaaggagt atgagtactc     600
agtggagtgc caggaggaca gtgcctgccc agctgctgag gagagtctgc ccattgaggt     660
catggtggat gccgttcaca agctcaagta tgaaaactac accagcagct tcttcatcag     720
ggacatcatc aaacctgacc cacccaagaa cttgcagctg aagccattaa agaattctcg     780
gcaggtggag gtcagctggg agtaccctga cacctggagt actccacatt cctacttctc     840
cctgacattc tgcgttcagg tccagggcaa gagcaagaga gaaaagaaag atagagtctt     900
cacggacaag acctcagcca cggtcatctg ccgcaaaaat gccagcatta gcgtgcgggc     960
ccaggaccgc tactatagct catcttggag cgaatgggca tctgtgccct gcagttaggt    1020
```

-continued

```
tctgatccag gatgaaaatt tggagg                                        1046

<210> SEQ ID NO 6
<211> LENGTH: 1729
<212> TYPE: DNA
<213> ORGANISM: Artificial Sequence
<220> FEATURE:
<223> OTHER INFORMATION: Synthetic

<400> SEQUENCE: 6
cgcgcggccg cgccaccatg tgtcaccagc agttggtcat ctcttggttt tccctggttt    60
ttctggcatc tccctcgtg gccatatggg aactgaagaa agatgtttat gtcgtagaat    120
tggattggta tccggatgcc cctggagaaa tggtggtcct cacctgtgac accccctgaag   180 aagatggtat cacctggacc ttggaccaga gcagtgaggt cttaggctct ggcaaaaccc    240
tgaccatcca agtcaaagag tttggagatg ctggccagta cacctgtcac aaaggaggcg    300
aggttctaag ccattcgctc ctgctgcttc acaaaaagga agatggaatt tggtccactg    360
atattttaaa ggaccagaaa gaacccaaaa ataagacctt tctaagatgc gaggccaaga    420
attattctgg acgtttcacc tgctggtggc tgacgacaat cagtactgat ttgacattca    480
gtgtcaaaag cagcagaggc tcttctgacc cccaaggggt gacgtgcgga gctgctacac    540
tctctgcaga gagagtcaga ggggacaaca aggagtatga gtactcagtg gagtgccagg    600
aggacagtgc ctgcccagct gctgaggaga gtctgcccat tgaggtcatg gtggatgccg    660
ttcacaagct caagtatgaa aactacacca gcagcttctt catcagggac atcatcaaac    720
ctgacccacc caagaacttg cagctgaagc cattaaagaa ttctcggcag gtggaggtca    780
gctgggagta ccctgacacc tggagtactc cacattccta cttctccctg acattctgcg    840
ttcaggtcca gggcaagagc aagagagaaa agaaagatag agtcttcacg gacaagacct    900
cagccacggt catctgccgc aaaaatgcca gcattagcgt gcgggcccag gaccgctact    960
atagctcatc ttggagcgaa tgggcatctg tgccctgcag tggaggtggc ggtggaggct   1020
ccgcggctcg ccctgtgtcc ctgcagtgcc ggctcagcat gtgtccagcg cgcagcctcc   1080
tccttgtggc taccctggtc ctcctggacc acctcagttt ggccagaaac ctccccgtgg   1140
ccactccaga cccaggaatg ttcccatgcc ttcaccactc ccaaaacctg ctgagggccg   1200
tcagcaacat gctccagaag gccagacaaa ctctagaatt ttacccttgc acttctgaag   1260
agattgatca tgaagatatc acaaaagata aaaccagcac agtggaggcc tgtttaccat   1320
tggaattaac caagaatgag agttgcctaa attccagaga gacctctttc ataactaatg   1380
ggagttgcct ggcctccaga aagacctctt ttatgatggc cctgtgcctt agtagtattt   1440
atgaagactt gaagatgtac caggtggagt tcaagaccat gaatgcaaag cttctgatgg   1500
atcctaagag gcagatcttt ctagatcaaa acatgctggc agttattgat gagctgatgc   1560
aggccctgaa tttcaacagt gagactgtgc cacaaaaatc ctcccttgaa gaaccggatt   1620
tttataaaac taaaatcaag ctctgcatac ttcttcatgc tttcagaatt cgggcagtga   1680
ctattgatag agtgatgagc tatctgaatg cttcctaagc ggccgccgc               1729
```